US010983128B2

(12) United States Patent
Bahjat et al.

(10) Patent No.: US 10,983,128 B2
(45) Date of Patent: Apr. 20, 2021

(54) CXCL11 AND SMICA AS PREDICTIVE BIOMARKERS FOR EFFICACY OF ANTI-CTLA4 IMMUNOTHERAPY

(71) Applicants: BRISTOL-MYERS SQUIBB COMPANY, Princeton, NJ (US); Providence Health & Services, Portland, OR (US)

(72) Inventors: Keith Sadoon Bahjat, Portland, OR (US); Helena Maria Hoen, Portland, OR (US); Yoshinobu Koguchi, Portland, OR (US); Alan J. Korman, Piedmont, CA (US)

(73) Assignees: BRISTOL-MYERS SQUIBB COMPANY, Princeton, NJ (US); Providence Health & Services, Portland, OR (US)

( * ) Notice: Subject to any disclaimer, the term of this patent is extended or adjusted under 35 U.S.C. 154(b) by 243 days.

(21) Appl. No.: 15/547,304

(22) PCT Filed: Feb. 5, 2016

(86) PCT No.: PCT/US2016/016769
§ 371 (c)(1),
(2) Date: Jul. 28, 2017

(87) PCT Pub. No.: WO2016/127052
PCT Pub. Date: Aug. 11, 2016

(65) Prior Publication Data
US 2018/0246113 A1    Aug. 30, 2018

Related U.S. Application Data

(60) Provisional application No. 62/220,726, filed on Sep. 18, 2015, provisional application No. 62/112,359, filed on Feb. 5, 2015.

(51) Int. Cl.
*A61K 39/00*     (2006.01)
*G01N 33/574*    (2006.01)
*C07K 16/28*     (2006.01)
*A61K 39/395*    (2006.01)
*A61K 45/06*     (2006.01)
*C07K 16/30*     (2006.01)

(52) U.S. Cl.
CPC .  *G01N 33/57492* (2013.01); *A61K 39/39558* (2013.01); *A61K 45/06* (2013.01); *C07K 16/2818* (2013.01); *C07K 16/30* (2013.01); *G01N 33/5743* (2013.01); *G01N 33/57488* (2013.01); *A61K 2039/505* (2013.01); *A61K 2039/54* (2013.01); *A61K 2039/545* (2013.01); *A61K 2039/55* (2013.01); *C07K 2317/21* (2013.01); *C07K 2317/76* (2013.01); *G01N 2333/521* (2013.01); *G01N 2333/70539* (2013.01); *G01N 2800/52* (2013.01)

(58) Field of Classification Search
CPC ................................................. A61K 2039/505
See application file for complete search history.

(56) References Cited

FOREIGN PATENT DOCUMENTS

WO    2011/045704 A1    4/2011
WO    2014/064240 A1    5/2014

OTHER PUBLICATIONS

Hodi, S. et al., "Improved Survival with Ipilimumab in Patients with Metastatic Melanoma," The New England Journal of Medicine, vol. 363(8): 711-723 (2010).
International Preliminary Report on Patentability, PCT/US2016/016769, dated Aug. 8, 2017, 7 pages.
International Search Report and Written Opinion, PCT/US2016/016769, dated Jun. 1, 2016, 11 pages.
Jinushi, M et al., "Therapy-induced antibodies to MHC class I chain-related protein A antagonize immune suppression and stimulate antitumor cytotoxicity," PNAS, US, vol. 103 (24): 9190-9195 (2006).
Koguchi, Y. et al., "Serum immunoregulatory proteins as predictors of overall survival of metastatic melanoma patients treated with ipilimumab," Journal for Immunotherapy of Cancer, vol. 3(2): 1 page (2015).
Rebmann, V. et al., "Soluble MICA as an independent prognostic factor for the overall survival and progression-free survival of multiple myeloma patients," Clinical Immunology, vol. 123(1):114-120(2007).
Ji, R. et al., "An immune-active tumor microenvironment favors clinical response to ipilimumab," Cancer Immunology, Immunotherapy, vol. 61(7):1019-1031 (2012).

*Primary Examiner* — Stephen L Rawlings
(74) *Attorney, Agent, or Firm* — Nelson Mullins Riley & Scarborough LLP; Jane E. Remillard, Esq.; Christopher L. Frank

(57)    ABSTRACT

Provided herein are methods for selecting a cancer patient for anti-CTLA-4 immunotherapy, or predicting whether a cancer patient will respond to anti-CTLA4 immunotherapy, based on measured levels of CXCL1 1 and/or sMICA. Such methods are useful for determining whether an anti-CTLA-4 immunotherapy is likely to improve overall survival of a cancer patient. Also provided herein are methods of treating a cancer patient with an anti-CTLA-4 immunotherapy, wherein the patient is first tested for levels of CXCL1 1 and/or sMICA. Also provided are methods for treating a cancer patient with a CXCL1 1 antagonist or sMICA ant agonist alone, or in combination with each other and/or with additional anti-cancer agents, such as a CTLA-4 antagonist.

16 Claims, 15 Drawing Sheets
Specification includes a Sequence Listing.

ID
CXCL11 AND SMICA AS PREDICTIVE BIOMARKERS FOR EFFICACY OF ANTI-CTLA4 IMMUNOTHERAPY

REFERENCE TO RELATED APPLICATIONS

This application is a 35 U.S.C. 371 national stage filing of International Application No. PCT/US2016/016769, filed Feb. 5, 2016, which claims priority to U.S. Provisional Application No. 62/112,359, entitled "Soluble Immunoregulatory Proteins as Predictors of Overall Survival of Advanced Melanoma Patient", filed on Feb. 5, 2015, and U.S. Provisional Application No. 62/220,726, entitled "CXCL11 and SMICA as Predictive Biomarkers for Efficacy of Anti-CTLA4 Immunotherapy", filed Sep. 18, 2015. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Aug. 29, 2019, is named MXI_542US_Substitute_Sequence_Listing.txt and is 3,537 bytes in size.

BACKGROUND

Ipilimumab is a human monoclonal antibody that specifically binds to cytotoxic T lymphocyte antigen-4 (CTLA-4). CTLA-4 is expressed on activated T cells, has structural similarities to the costimulatory molecule CD28, and binds to the same ligands as CD28, albeit with higher affinity. Binding of CTLA-4 to CD80/CD86 inhibits T cell activation by limiting interleukin-2 (IL-2) production and expression of the IL-2 receptor (CD25) (Wolchok et al., *Annals of the New York Academy of Sciences* 2013; 1291:1-13). Ipilimumab prevents CTLA-4 from binding its ligands, thereby promoting activation of effector T cells via prolonged CD28 signaling (Rudd et al., *Immunol Rev* 2009; 229:12-26). In addition, anti-CTLA-4 antibodies can deplete intratumoral regulatory T cells, subverting yet another mechanism of immunosuppression (Simpson et al., *J Exp Med* 2013; 210:1695-1710).

Ipilimumab was approved in the United States for the treatment of metastatic melanoma in 2011. While a significant breakthrough in the treatment of metastatic melanoma, there is a need to increase the percentage of patients who achieve a response to treatment, such as prolonged overall survival.

Unlike traditional cancer therapies, immunotherapeutics act primarily upon cells of the immune system. The requirement for the immune system as a third-party mediator of the drug's activity suggests the balance of positive and negative regulators of the immune response at the time of therapy may be a critical determinant of efficacy for any immunotherapy. Cytokines, chemokines, and soluble receptors regulate the survival, activity, and location of immune effector cells and thus represent potential players in determining drug efficacy. Of particular interest are soluble factors involved in the recruitment and regulation of effector T cells representing the most readily measurable clinical biomarkers. With an increasing number of treatment options available and increased use of targeted therapies, predictive biomarkers that identify those patients most likely to benefit from a specific treatment would be highly beneficial.

SUMMARY

Provided herein are methods for optimizing treatment of a cancer patient (e.g., a patient diagnosed with metastatic melanoma) with an anti-CTLA-4 immunotherapy. These methods include a) selecting a cancer patient for treatment with an anti-CTLA-4 immunotherapy, or b) predicting the responsiveness of a cancer patient for treatment with an anti-CTLA-4 immunotherapy, or c) treating a cancer patient with anti-CTLA-4 immunotherapy, by determining whether the patient is likely to benefit from treatment with an anti-CTLA-4 immunotherapy (e.g., a CTLA-4 antagonist).

In one embodiment, the determination is based on measuring the level of CXCL11 and/or sMICA in a biological sample from the patient, and comparing the level with a threshold level, wherein levels of CXCL11 and/or sMICA below the threshold level is indicative that the patient is likely to respond to anti-CTLA-4 immunotherapy, and levels above the threshold level is indicative that the patient is unlikely to respond to anti-CTLA-4 immunotherapy. If the levels of CXCL11 and/or sMICA are below the threshold level, then the patient a) is selected for treatment with an anti-CTLA-4 immunotherapy, or b) predicted to be responsive to anti-CTLA-4 immunotherapy.

In another embodiment, the determination is based on measuring the level of CXCL11 and/or sMICA in a biological sample from the patient, and if the levels of CXCL11 and/or sMICA are below the threshold level, then the patient is administered a therapeutically effective amount of an anti-CTLA-4 immunotherapy. Alternatively, the determination is based on obtaining the levels of CXCL11 and/or sMICA in a biological sample from the patient, and if the levels of CXCL11 and/or sMICA are below a threshold level, then the patient is administered a therapeutically effective amount of an anti-CTLA4 immunotherapy, or administration of a therapeutically effective amount of an anti-CTLA4 immunotherapy is ordered.

In another embodiment, the patient is further administered a therapeutically effective amount of a CXCL11 antagonist and/or sMICA antagonist. Alternatively, administration of a therapeutically effective amount of a CXCL11 antagonist and/or sMICA antagonist is ordered. Administration of the CXCL11 antagonist and/or sMICA antagonist, or the order to administer the CXCL11 antagonist and/or sMICA antagonist, can be concurrent with, or sequential to, administration of the anti-CTLA-4 immunotherapy.

In another embodiment, the CXCL11 antagonist and/or sMICA antagonist is a protein (e.g., an antibody or antigen-binding portion thereof), small molecule, or nucleic acid.

In another embodiment, the step of determining the level of CXCL11 and/or sMICA in a biological sample from the patient involves determining the level of CXCL11 and/or sMICA protein or gene expression. For example, the level of CXCL11 or sMICA is determined by contacting the biological sample from the patient with an agent that binds to CXCL11 or sMICA, respectively (e.g., an anti-CXCL11 antibody or anti-sMICA antibody or antigen-binding portion thereof), and detecting the binding of the agent to CXCL11 or sMICA in the biological sample (e.g., serum).

In another embodiment, the threshold level for CXCL11 is about 35 pg/mL, as measured by bead assay, and/or the threshold level for sMICA is about 247 pg/mL, as measured by a bead-based immunoassay.

The methods of the present invention can be applied to patients diagnosed with various types of cancer, e.g., melanoma, and/or wherein the cancer is a metastatic cancer, refractory cancer, or recurrent cancer.

In another embodiment, the method includes administering one or more additional therapeutics and/or includes cancer patients that have previously failed at least one non-CTLA-4-based therapy, e.g., administration of IL-2, dacarbazine, or temozolomide.

In another embodiment, the anti-CTLA-4 immunotherapy is an anti-CTLA-4 antibody, such as, ipilimumab or tremelimumab, which is administered to the patient at various dosages (e.g., at between 1 mg/kg to 10 mg/kg, at 3 mg/kg, or at 10 mg/kg) and intervals (e.g., every 1 to 4 weeks, every 3 weeks, 4 times, or 1, 2, 3, 4, 5, 6, 7, 8, 9, or 10 times or more).

Other features and advantages of the instant disclosure will be apparent from the following detailed description and examples, which should not be construed as limiting.

BRIEF DESCRIPTION OF THE FIGURES

FIGS. 6A, 6C, and 6E represent the gp100 treated group. FIGS. 6B, 6D, and 6F correspond to the ipilimumab treated group.

DETAILED DESCRIPTION

Overview

Figure 1:
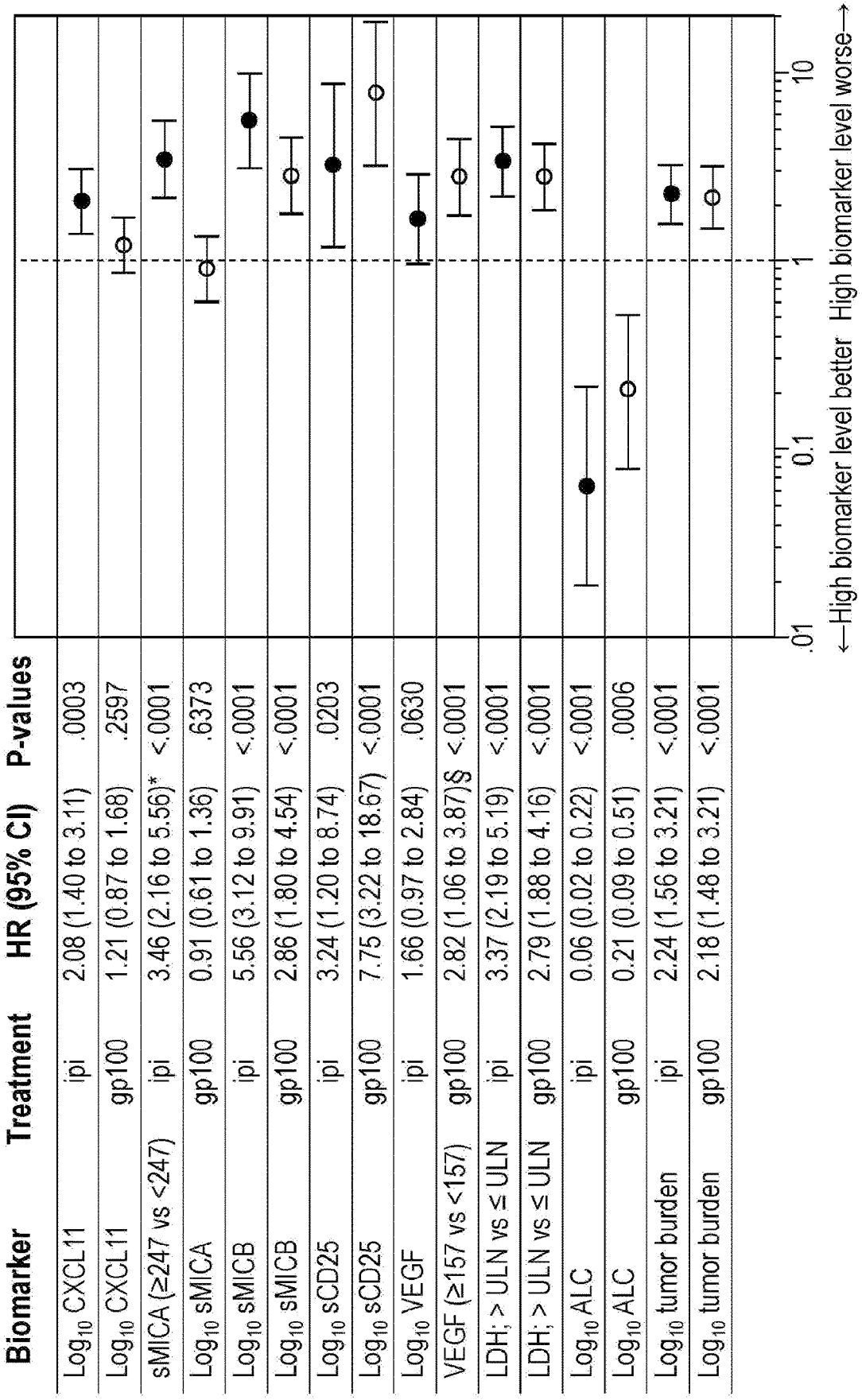
FIG. 1 shows the results of the univariate analysis of biomarker effects on overall survival (OS) for patients from the phase 3 clinical trial. Hazard ratios (HRs) and confidence intervals (CIs) are shown for the association with overall survival of patients treated with ipilimumab (ipi) or gp100. Cox proportional hazards regression was used for univariate analysis of biomarker effects on OS. HR is numerator vs. denominator. Among 124 patients analyzed, 35 were censored in the ipilimumab-treated group. Among 123 patients analyzed, 13 were censored in the gp100-treated group. CXCL11, sCD25, VEGF—5 missing in the gp100 group and 11 missing in the ipilimumab group. *In quadratic effects model of the ipilimumab group, $(\log_{10} \text{sMICA})^2$ P<0.0001; in gp100 group, $(\log_{10} \text{VEGF})^2$ P=0.0002.

The present invention is based, at least in part, on the discovery that low baseline serum CXCL11 and sMICA levels are associated with improved overall survival in metastatic melanoma patients treated with a CTLA-4 antagonist, but not in patients treated with a "control" gp100 vaccine. The measurement of pretreatment serum CXCL11 and sMICA levels can thus identify patients most likely to benefit from (i.e., respond to) anti-CTLA-4 immunotherapy. Because certain melanoma patients fail to respond to anti-CTLA-4 immunotherapy, avoiding treatment of such refractory patients would reduce exposure to inefficient therapy, eliminate their risks for adverse effects, and lower overall costs of therapy.

Definitions

In order that the present description may be more readily understood, certain terms are first defined. Additional definitions are set forth throughout the detailed description.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen. Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., *Nature* 1989; 341:544-6), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 1988; 242:423-6; and Huston et al., *PNAS* 1998; 85:5879-83). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg, *Nature Biotech* 2005; 23:1117-25), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species (e.g., human variable regions) and the constant regions are derived from another species (e.g., mouse constant regions), such as an antibody in which the variable regions are derived from a mouse antibody and the constant regions are derived from a human antibody. Constant region sequences for various species are known in the art and could be readily obtained by the skilled artisan to generate chimeric antibodies.

An "isolated antibody," as used herein, is intended to refer to an antibody which is substantially free of other antibodies having different antigenic specificities.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. A "protein" may comprise one or more polypeptides.

As used herein, "cytotoxic T lymphocyte-associated antigen-4," "CTLA-4," "CTLA4," "CTLA-4 antigen" and "CD152" (see, e.g., Murata, *Am J Pathol* 1999; 155:453-60) are used interchangeably, and include variants, isoforms, species homologs of human CTLA-4, and analogs having at least one common epitope with CTLA-4 (see, e.g., Balzano, *Int J Cancer Suppl* 1992; 7:28-32). "CTLA-4 protein" is intended to encompass full-length CTLA-4 protean, CTLA-4 protein fragments, CTLA-4 protein variants, and CTLA-4 fusion proteins (e.g. CTLA-4/Fc fusion protein), which an anti-CTLA-4 antibody (e.g., ipilimumab) can bind.

"Ipilimumab" (also referred to as MDX-010, MDX-101, 10D1, and Yervoy®) refers to a fully human IgG1 anti-CTLA-4 antibody that blocks the binding of CTLA-4 to CD38 and CD86 expressed on antigen presenting cells, thereby blocking the negative down-regulation of the immune responses elicited by e interaction between these molecules. Ipilimumab comprises the following heavy and light chain variable region sequences.

```
ipilimumab VH
                                        (SEQ ID NO: 1)
QVQLVESGGGVVQPGRSLRLSCAASGFTFSSYTMHRQAPGKGLEWV

TFISYDGNNKYYADSVKGRFTISRDNSKNTLYLQMNSLRAEDTAIY

YCARTGWLGPFDYWGQGTLVTVSS ipilimumab VL
                                        (SEQ ID NO: 2)
EIVLTQSPGTLSLSPGERATLSCRASQSVGSSYLAWYQQKPGQAPR

LLIYGAFSRATGIPDRFSGSGSGTDFTLTISRLEPEDFAVYYCQQY

GSSPWTFGQGTKVEIK
```

Ipilimumab can also be referred to by its CAS Registry No. 477202-00-9, and is disclosed as antibody 10D1 in PCT Publication No. WO 01/14424, the content of which is herein incorporated by reference. As used herein, ipilimumab also is intended to encompass antibodies comprising the variable region or CDR sequences of ipilimumab.

Initial studies in patients with melanoma showed that ipilimumab could cause objective durable tumor regressions (Phan et al, *PNAS* 2003; 100:8372-7). Also, reductions of serum tumor markers were seen for some patients with ovarian or prostate cancer (Hodi et al., *PNAS* 2003; 100: 4712-7). Iipilimumab also has antitumor activity in patients with advanced melanoma (Weber et al, *J Clin Oncol* 2008; 26:5950-6; Weber, *Cancer Immunol Immunother* 2009; 58:823-30).

"CXCL11," also known as interferon-inducible T cell α chemoattractant (I-TAC), H174, b-R1, interferon-γ inducible protein 9 (IP-9), small inducible cytokine B11 (SCYB11), and SCYB9B, is a 94 amino acid polypeptide with the nucleotide and amino acid sequences (human) set forth in Genbank Accession No. NM005409 and Genbank Accession No. NP005400 (SEQ ID NO: 3), respectively. CXCL11 is intended to encompass full-length CXCL11 protein, CXCL11 protein fragments, CXCL11 protein variants, and CXCL11 fusion proteins. CXCL11 is known to bind to two alternative receptors, CXCR3 and CXCR7 (Colvin et al., JBC 2004; 279:30219-27; Burns et al., *J Exp Med* 2006; 203:2201-13). High levels of CXCL11 are protective in patients with renal cell carcinoma (Kondo et al., *Cancer Sci* 2006; 97:780-6), and low levels of CXCL11 are associated with poor prognosis in patients with gastric carcinoma (Pasini et al., *J Gastroenterol* 2014; 49:1453-66). These reports suggest that low levels of CXCL11 may be detrimental in cancer patients and associated with poor prognosis.

As used herein, "MICA," also known as MIC-A and PERB11.1, is a ligand for the immunoreceptor natural killer group 2, member D (NKG2D). The nucleotide and amino acid sequences of human MICA are set forth in Genbank Accession No. NM000238 and Genbank Accession No. NP000238, respectively. MICA is intended to encompass full-length MICA protein, MICA protein fragments (e.g., soluble MICA), MICA protein variants, various MICA alleles, and MICA fusion proteins. High levels of sMICA are found in many cancers, including hematopoietic malignancies, epithelial cancers, colorectal cancer, liver cancer, prostate cancer, and melanoma (Champsaur and Lanier, *Immunological Reviews* 2010; 235:267-85). sMICA is generated through various mechanisms, such as shedding due to the activities of metalloproteases, ADAM family of proteases (e.g., ADAM10 and ADAM17), and thiol disulphide isomerases (e.g., ERp5) (Champsauer and Lanier, supra).

As used herein, "antagonist" refers to any molecule that partially or fully inhibits or neutralizes a biological activity of a polypeptide, such as CXCL11 or soluble MICA (sMICA), or that partially or fully inhibits the transcription or translation of a nucleic acid encoding the polypeptide. Exemplary antagonist molecules include, but are not limited to, antibodies, polypeptide fragments, oligopeptides, organic molecules (including small molecules), and nucleic acids (e.g., anti-sense nucleic acids).

As used herein, "CXCL11 antagonist" refers to an agent that inhibits CXCL11 activity, e.g., an agent that disrupts CXCL11 binding to its receptors CXCR3 and/or CXCR7, or an agent that reduces the protein or mRNA levels of CXCL11. In certain embodiments, the CXCL11 antagonist is an antibody.

As used herein, "sMICA antagonists" refers to an agent that inhibits sMICA activity, e.g., an agent that inhibits (partially or completely) sMICA binding to NKG2D, an agent that leads to reduced shedding of sMICA from MICA, an agent that inhibits MICA-induced NGKD downregulation and diminished NK cell cytotoxicity, or an agent that reduces the levels of sMICA. In certain embodiments, the sMICA antagonist is an antibody that binds to MICA (e.g., sMICA), such as an antibody described in WO2014/144791, the contents of which are herein incorporated by reference. In a further embodiment, the antibody binds to the alpha 3 domain of MICA, and thus does not block NKG2D receptor binding.

As used herein, a "small molecule" refers to an agent with a molecular weight less than about 6 kDa, for example, less than about 2.5 kDa. Small molecules can be obtained from small chemical libraries, peptide libraries, or collections of natural products.

As used herein, "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

As used herein, "immunomodulator" or "immunoregulator" refers to an agent, e.g., a component of a signaling pathway, that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

As used herein, "immunotherapy" refers to the treatment of a subject afflicted with, or at risk of contracting or suffering a recurrence of, a disease by a method comprising inducing, enhancing, suppressing or otherwise modifying an immune response. In this context, "anti-CTLA-4 immunotherapy" refers to the treatment of a subject afflicted with, or at risk of developing or suffering a recurrence of, a disease (e.g., cancer) by a method comprising inducing, enhancing, suppressing or otherwise modifying an immune response by administering an agent (e.g., an anti-CTLA-4 antibody such as ipilimumab) that modulates CTLA-4 signaling and results in, e.g., the induction and/or enhancement of T cell activation (e.g., increase in IL-2 and/or IFN-γ production by T cells and/or increase in proliferation of T cells), depletion of regulatory T cells, etc.

As used herein, "potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

As used herein, "hematological malignancy" includes a lymphoma, leukemia, myeloma or a lymphoid malignancy, as well as a cancer of the spleen and the lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

As used herein, a "tumor" refers to an abnormal mass of tissue resulting from excessive cell division that is uncontrolled and progressive. Tumors can be benign or malignant.

As used herein, "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc. Various aspects described herein are described in further detail in the following subsections.

As used herein, "biological sample" refers to cells (e.g., tumor cells, T cells, B cells or other), tissues (e.g., tumor), fluids (e.g., serum or plasma), and/or combination thereof isolated from a subject.

As used herein, "control sample" or "reference sample" as used herein refers to any clinically relevant control or reference sample, including, e.g., a sample from a healthy subject or a population of healthy subjects, or a sample from a patient treated with an agent that is different from the agent of interest. For example, in some embodiments, an intervention group comprises cancer patients treated with ipilimumab, and the control group comprises cancer patients treated with a gp100 vaccine.

As used herein, "normal," when used in the context of the term "subject" or "patient," refers to an individual or group of individuals who do not have a particular disease or condition (e.g., cancer), and is not suspected of having or being at risk for developing the disease or condition.

As used herein, "biomarker" refers to a distinctive biological or biologically derived indicator of a process, event or conditions. In certain embodiments, the biomarker is a gene or gene product (i.e., a polypeptide).

As used herein, "predictive biomarker" as used herein refers to a biomarker that can be used in advance of therapy to estimate the likelihood or predictability of response to a given therapeutic agent or class of therapeutic agents. In certain embodiments, the therapeutic agent is an anti-CTLA-4 immunotherapy, for example, an anti-CTLA-4 antibody. In some embodiments, the predictive biomarker is CXCL11. In other embodiments, the predictive biomarker is sMICA.

As used herein, "threshold level" refers to a level of biomarker expression, above which a patient is predicted to respond to anti-CTLA-4 immunotherapy and below which a patient is predicted to be unresponsive to anti-CTLA-4 immunotherapy. The threshold level may be based on one or more compilations of data from patient samples that have received anti-CTLA-4 immunotherapy and determined to be responsive or unresponsive.

As used herein, the term "obtaining," when used in reference to levels of CTLA-4 and/or sMICA, refers to the direct or indirect procurement of the levels of CTLA-4 and/or sMICA. The levels of CTLA-4 and/or sMICA can be directly measured by laboratory personnel. In some embodiments, the levels of CTLA-4 and/or sMICA measured by laboratory personnel can be made available to at least one other party, such as a medical practitioner, as data in written or electronic format. In this context, a second party "obtains" the levels of CTLA-4 and/or sMICA by consulting the data.

As used herein, "treat," "treating," and "treatment," refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, intratracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. In other preferred embodiments described herein, tumor regression may be observed and may continue for a period of at least about 20 days, more preferably at least about 40 days, or even more preferably at least about 60 days.

As used herein, a "refractory cancer" (also known as a "resistant" cancer) is a cancer that does not respond to treatment (e.g., the cancer may be resistant at the beginning of treatment or it becomes resistant during treatment). As used herein, a "non-responder" is a subject who does not respond to treatment. A "responder" is a subject who responds to treatment (e.g., demonstrates some beneficial effect in response to treatment, such as amelioration of at least one symptom of a disease or disorder).

It is to be noted that the term "a" or "an" entity refers to one or more of that entity; for example, "a polynucleotide", is understood to represent one or more polynucleotides. As such, the terms "a" (or "an"), "one or more", and "at least one" can be used interchangeably herein.

The term "about" as used herein when referring to a measurable value such as an amount, temporal duration, and the like, encompasses variations of up to ±10% from the specified value. Unless otherwise indicated, all numbers expressing quantities of ingredients, properties such as molecular weight, reaction conditions, scores in an art-recognized scoring system, etc., used herein are understood as being modified by the term "about."

Various aspects described herein are described in further detail in the following subsections.

I. Patient Population

Provided herein are methods for selecting a cancer patient for anti-CTLA-4 immunotherapy. In particular, selection of the cancer patient is based on the levels of CXCL11 and/or sMICA in the patient. As demonstrated in the Examples, low CXCL11 and sMICA protein levels are associated with response to anti-CTLA-4 immunotherapy and improved overall survival of cancer patients.

Accordingly, in one aspect, provided herein are methods of selecting a cancer patient for treatment with an anti-CTLA-4 immunotherapy comprising:

(a) determining the level of CXCL11 and/or sMICA in a biological sample from the patient;

(b) comparing the level with a threshold level, wherein levels of CXCL11 and/or sMICA below the threshold level is indicative that the patient is likely to respond to anti-CTLA-4 immunotherapy, and levels above the threshold level is indicative that the patient is unlikely to respond to anti-CTLA-4 immunotherapy, (c) if the levels of CXCL11 and/or sMICA are below the threshold level, then selecting the patient for treatment with an anti-CTLA-4 immunotherapy.

In another aspect, provided herein are methods for predicting the responsiveness of a cancer patient to anti-CTLA-4 immunotherapy comprising:

(a) determining the level of CXCL11 and/or sMICA in a biological sample from the patient;

(b) comparing the level with a threshold level, wherein levels of CXCL11 and/or sMICA below the threshold level is indicative that the patient is likely to respond to anti-CTLA-4 immunotherapy and levels above the threshold level is indicative that the patient is unlikely to respond to anti-CTLA-4 immunotherapy, (c) if the levels of CXCL11 and/or sMICA are below the threshold level, then predicting the patient will be responsive to anti-CTLA-4 immunotherapy.

In some embodiments, the level of either CXCL11 or sMICA is used to select a cancer patient for anti-CTLA-4 immunotherapy or predict the responsiveness of a patient to anti-CTLA-4 immunotherapy. In other embodiments, the levels of both CXCL11 and sMICA are used to determine whether a cancer patient will benefit from anti-CTLA-4 immunotherapy or predict the responsiveness of a patient to anti-CTLA-4 immunotherapy.

In some embodiments, elevated levels of CXCL11 and/or sMICA in a biological sample obtained from a cancer patient, relative to the level of CXCL11 and/or sMICA in a normal control sample (e.g., a healthy individual or population of healthy individuals), indicates the cancer patient is unlikely to respond to anti-CTLA-4 immunotherapy.

In other embodiments, a reduction in the level of CXCL11 and/or sMICA in a biological sample from a cancer patient, relative to the level of CXCL11 and/or sMICA in a normal control sample (e.g., a healthy individual or population of healthy individuals), indicates the cancer patient is likely to respond to (i.e., is a candidate for) anti-CTLA-4 immunotherapy.

As shown in the Examples, a CXCL11 protein level less than about 35 pg/mL, and/or a sMICA protein level less than about 247 pg/mL, is associated with response to anti-CTLA-4 immunotherapy. Accordingly, provided herein is a method for selecting a patient for anti-CTLA-4 immunotherapy, wherein, if the patient has a CXCL11 protein level less than about 35 pg/mL, and/or an sMICA protein level less than about 247 pg/mL, the patient is considered likely to respond to anti-CTLA-4 immunotherapy, and is thus selected for anti-CTLA-4 immunotherapy (e.g., treatment with ipilimumab or tremelimumab). In certain embodiments, the protein levels of CXCL11 and/or sMICA are measured in patient serum. In one embodiment, the protein levels of CXCL11 and/or sMICA are determined using a bead-based assay.

In particular embodiments, a cancer patient having a protein level of CXCL11 between about 0 pg/mL to about 40 pg/mL, between about 5 pg/mL to about 40 pg/mL, between about 10 pg/mL to about 40 pg/mL, between about 15 pg/mL to about 40 pg/mL between about 20 pg/mL to about 40 pg/mL, between about 25 pg/mL to about 40 pg/mL between about 30 pg/mL to about 40 pg/mL, or between about 35 pg/mL to about 40 pg/mL, is selected for anti-CTLA-4 immunotherapy, or is predicted to be responsive to anti-CTLA-4 immunotherapy.

In further embodiments, the threshold level of sMICA is between about 0 pg/mL to about 250 pg/mL, between about 25 pg/mL to about 250 pg/mL, between about 50 pg/mL to about 250 pg/mL, between about 75 pg/mL to about 250 pg/mL between about 100 pg/mL to about 250 pg/mL, between about 125 pg/mL to about 250 pg/mL between about 150 pg/mL to about 250 pg/mL, between about 175 pg/mL to about 250 pg/mL, between about 200 pg/mL to about 250 pg/mL, or between about 225 pg/mL to about 250 pg/mL, is selected for anti-CTLA-4 immunotherapy, or is predicted to be responsive to anti-CTLA-4 immunotherapy.

In some embodiments, the control sample is obtained from an individual who does not have cancer, and is not suspected of being at risk of developing cancer. In other embodiments, the control sample can be pooled from at least one, such as at least two, at least three, at least four, at least five, at least six, at least seven, at least eight, at least nine, or at least 10 healthy individuals or individuals who do not have or are not suspected of being at risk of developing cancer.

In another aspect, provided herein are methods of ordering the treatment of a cancer in a patient comprising:

(a) obtaining the level of CXCL11 and/or sMICA measured in a biological sample from a patient, and (b) if the level of CXCL11 is less than about 35 pg/mL and/or the level of sMICA is less than about 247 pg/mL, then ordering the administration of a therapeutically effective amount of an anti-CTLA-4 immunotherapy to the patient.

In some embodiments, the measured values of CXCL11 and/or sMICA are recorded in writing or on a computer readable medium. The method may also involve communicating the measured value of CXCL11 and/or sMICA to the patient and/or medical practitioner who cares for the patient.

In other embodiments, a medical practitioner receives information regarding the levels of CXCL11 and/or sMICA from a first practitioner in order to make a determination of whether the patient is likely to be responsive to anti-CTLA-4 immunotherapy.

In some embodiments, the subject has a cancer selected from the group consisting of squamous cell carcinoma, small-cell lung cancer, non-small cell lung cancer, squamous non-small cell lung cancer (NSCLC), non squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio-immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscaroma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. In a particular embodiment, the patient has melanoma.

In certain embodiments, the cancer is a metastatic cancer, refractory cancer, or recurrent cancer.

II. Methods of Measuring Biomarkers

The levels (protein or RNA) of CXCL11 and/or sMICA in a biological sample can be determined (measured) using any suitable method known in the art (see, e.g., Harlow and Lane (1988) Antibodies: A Laboratory Manual," Cold Spring Harbor Laboratory: Cold Spring Harbor, N.Y.). In general, protein levels are determined by contacting a biological sample with an agent that binds to CXCL11 or sMICA, detecting the levels of CXCL11 or sMICA in the sample, and comparing the levels of CXCL11 or sMICA in the sample with the levels of CXCL11 or sMICA in a control sample.

Non-limiting examples of binding agents that are suitable for determining the levels of CXCL11 or sMICA are monoclonal and polyclonal antibodies specific for CXCL11 or sMICA, as well as antigen-binding fragments thereof (Fab fragments, scFvs, etc). Antibodies can be from commercial sources. If unavailable from commercial sources, art-recognized methods can be used to generate monoclonal antibodies, polyclonal antibodies, and fragments thereof.

Binding agents can be directly or indirectly labeled with a detectable moiety. Such moieties can facilitate the detection of CXCL11 and/or sMICA by allowing visualization of the complex formed between the binding agent and CXCL11 and/or sMICA in a biological sample. In some embodiments, the signal produced by the detectable moiety is measured and its intensity is proportional to the amount of CXCL11 and/or sMICA present in the sample being analyzed.

Exemplary detectable moieties include luminescent labels, fluorescent labels, radiolabels (e.g., $^{99}$Tc, $^{45}$Ti, $^{112}$In, $^{111}$In, $^{3}$H, $^{121}$I, $^{125}$I, $^{131}$I, $^{14}$C, $^{18}$F, $^{36}$Cl, $^{55}$Co, $^{58}$Co, $^{51}$Cr, $^{67}$Cu, $^{64}$Cu, $^{66}$Ga, $^{68}$Ga, $^{76}$Br, $^{89}$Zr, $^{35}$S, $^{32}$P, $^{90}$Y, $^{13}$N, $^{15}$O, $^{211}$At, $^{186}$Re, $^{188}$Re, $^{75}$Se), enzymatic labels (e.g., horseradish peroxidase, alkaline phosphatase, glucose oxidase, urease, acetylcholinetransferase, luciferase, and beta-galactosidase), epitope tags, chromophore labels, phosphorescent labels, photoaffinity molecules, ECL labels, dyes, biotin, haptens, and the like. Such labels are well known in the art and can be attached to the binding agents using art-recognized methods. Attachment of the detectable label does not interfere with binding of the agent to CXCL11 and/or sMICA. The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, methods of conjugating the labels result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter et al., *Curr Opin Chem Biol* 2009; 13 235-44; WO 2009/059278; WO 95/17886).

Depending on the biochemical nature of the moiety and the binding agent (e.g., antibody), different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger et al., *Angew Chem Int Ed Engl* 2008; 47:10030-74). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul et al., *Org Biomol Chem* 2009; 7:3361-71.

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese et al. *ChemBioChem* 2009; 10:425-7). It is also possible to obtain a desired amino acid modification by utilizing the specific enzymatic reactivity of certain enzymes with a natural amino acid in a given sequence context (see, e.g., Taki et al., *Prot Eng Des Sel* 2004; 17:119-26; Gautier et al. *Chem Biol* 2008; 15:128-36; Bordusa et al., *Bioorganic Chemistry* (2004) 389-403).

Site specific reaction and covalent coupling can also be achieved by the selective reaction of terminal amino acids with appropriate modifying reagents.

The reactivity of an N-terminal cysteine with benzonitrils (see Ren et al., *Angew Chem Int Ed Engl* 2009; 48:9658-62) can be used to achieve a site-specific covalent coupling.

Native chemical ligation can also rely on C-terminal cysteine residues (Taylor et al., *Nucleic Acids and Molecular Biology* 2009; 22:65-96). EP 1 074 563 describes a conjugation method which is based on the faster reaction of a cysteine within a stretch of negatively charged amino acids with a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see, e.g., de Graaf et al., *Bioconjug Chem* 2009; 20:1281-95). Since a great variety of orthogonal functional groups is at stake and can be introduced into a synthetic peptide, conjugation of such peptide to a linker is standard chemistry.

In some embodiments, the detectable label is indirectly conjugated to the antibody. For example, the antibody can be conjugated to biotin, and the label can be conjugated to avidin using methods well known in the art. In another embodiment, an unlabeled antibody is detected using a labeled antibody which binds to the unlabeled antibody. In certain embodiments, the labeled antibody that is used for detection is labeled with any of the labels set forth above.

In some embodiments, binding agents can be immobilized on a support or carrier, such as beads, latex particles, magnetic particles, microtiter plate well, cuvette, and the like). Exemplary carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, nylon, silk, and the like.

The methods used to determine CXCL11 and/or sMICA levels (protein or mRNA) in a biological sample can be qualitative, semi-quantitative, or quantitative. Art-recognized antibody-based methods for detecting protein levels in biological samples include, but are not limited to, enzyme-linked immunosorbent assay (ELISA), radioimmunoassays, electrochemiluninescence (ECL) assays, surface plasmon resonance, Western blot, immunoprecipitation, fluorescence-activated cell sorting (FACS), immunofluorescence, immunohistochemistry, latex agglutination, hemagglutination, mass spectrometry, bead assays, RT-PCR, quantitative PCR, and the like. Methods for determining CXCL11 and/or sMICA levels in a biological sample may include control samples (negative and positive controls). For example, a negative control sample may be a sample containing no CXCL11 and/or sMICA protein, and a positive controls sample is a sample containing CXCL11 and/or sMICA protein.

In a particular embodiment, a bead-based immunoassay is used to measure CXCL11 and/or sMICA protein levels. Bead-based immunoassays allow for the quantification of multiple proteins simultaneously. In one embodiment, a bead-based immunoassays involves the addition of color-coded beads that are precoated with an analyte-specific capture antibody for the target of interest (e.g., CXCL11 and/or sMICA) to a biological sample. This is followed by the addition of biotinylated detection antibody specific for the target of interest, thereby forming an antibody-antigen sandwich. Phycoerythrin-conjugated streptavidin is then added and the beads are read on a dual-laser flow-based detection instrument (e.g., Luminex 200™ or Bio-Rad® Bio-Plex® analyzer). See, e.g., rndsystems.com/resources/technical/luminex-bead-based-assay-principle. Bead-based immunoassays are commercially available from, e.g., R&D Systems (Luminex® Bead-based Multiplex Assay) and BD Biosciences (BD™ Cytometric Bead Array).

Methods for detecting and measuring protein expression can be performed in formats that allow for rapid preparation, processing, and analysis of multiple samples, e.g., through the use of multi-well assay plates or arrays.

In certain embodiments, the biological sample is whole blood. In other embodiments, the biological sample is serum. Additional non-limiting examples of biological samples are saliva, sputum, cerebrospinal fluid, urine, tears, or mucus. Biological samples for use in the methods described herein can be fresh or frozen. In some embodiments, CXCL11 and/or sMICA levels are determined from a combination of two or more, such as three, four, five, or six, different types of biological samples.

Biological samples can be obtained using any method known in the art, for example, blood collection followed by serum or plasma preparation, lavage, fine needle aspiration, swab, and phlebotomy. In some embodiments, biological samples are obtained from bone marrow.

III. Methods of Treatment

Once a cancer patient has been selected for anti-CTLA-4 immunotherapy using the methods described herein, the patient is treated with an anti-CTLA-4 immunotherapy, e.g., a therapeutic anti-CTLA-4 antibody. In some embodiments, the patient has failed at least one prior therapy (e.g., a therapy other than an anti-CTLA4 immunotherapy). For example, in one embodiment, the patient has failed IL-2 therapy. In another embodiment, the patient has failed dacarbazine therapy. In yet another embodiment, the patient has failed temozolomide therapy.

Accordingly, provided herein are methods of treating a cancer patient who has been selected for anti-CTLA-4 immunotherapy (according to the methods described herein) comprising administering to the patient a therapeutically-effective amount of an anti-CTLA-4 immunotherapy, e.g., a CTLA-4 antagonist that increases IL-2, increases IFN-γ production by T cells, and/or increases the proliferation of T cells and/or depletion of regulatory T cells. In a particular embodiment, the anti-CTLA-4 immunotherapy comprises administering an anti-CTLA-4 antibody, or an antigen-binding portion thereof. In one embodiment, the anti-CTLA-4 antibody is ipilimumab. In another embodiment, the anti-CTLA-4 antibody is tremelimumab.

Also provided herein are methods for treating cancer in a patient comprising:

(a) determining or obtaining the level of CXCL11 and/or sMICA measured in a biological sample from the patient, and (b) if the level of CXCL11 is below a threshold (e.g., less than about 35 pg/mL) and/or the level of sMICA is below a threshold (e.g., less than about 247 pg/mL), then administering to the patient a therapeutically effective amount of an anti-CTLA-4 immunotherapy.

In a particular embodiment, the patient has metastatic melanoma, and is treated with ipilimumab or tremelimumab.

Also provided herein are methods of treating a cancer patient who has been determined to have levels of CXCL11 and/or sMICA that are increased relative to a healthy individual (or population of healthy individuals). Such methods comprise administering a therapeutically effective amount of a CXCL11 and/or sMICA antagonist to the patient, regardless of whether the patient also receives anti-CTLA-4 immunotherapy. In some embodiments, the cancer patient is administered a CXCL11 and/or sMICA antagonist if the level of CXCL11 is above about 35 pg/mL and/or the level of sMICA is above about 247 pg/mL.

In some embodiments, the CXCL11 antagonist and/or sMICA antagonist inhibits the activity of CXCL11 and/or sMICA. In other embodiments, the CXCL11 antagonist and/or sMICA antagonist reduces the levels of CXCL11 and/or sMICA.

In some embodiments, a cancer patient determined to have levels of CXCL11 and/or sMICA that are increased relative to a healthy individual (or population of healthy individuals) is administered a CXCL11 antagonist and/or sMICA antagonist, and further administered an anti-CTLA-4 immunotherapy (e.g., ipilimumab or tremelimumab).

In further embodiments, the cancer patient is administered an anti-CTLA-4 immunotherapy and a CXCL11 and/or sMICA antagonist if the patient has levels of CXCL11 above about 35 pg/mL and/or levels of sMICA above about 247 pg/mL (e.g., in patient serum). In certain embodiments, the CXCL11 antagonist and/or sMICA antagonist is administered concurrently with the anti-CTLA-4 immunotherapy. In other embodiments, the CXCL11 antagonist and/or sMICA antagonist is administered separately (e.g., sequentially) with the anti-CTLA-4 immunotherapy.

Antagonists of CXCL11 and sMICA include, but are not limited to, small molecules, nucleic acids or nucleic acid analogs, proteins, peptides, oligopeptides, peptidomimetics, or a macromolecule that is not a nucleic acid or protein. Such molecules include, for example, peptide nucleic acid inhibitors, locked nucleic acid inhibitors, small interfering RNA, double stranded RNA, antisense compounds, L-RNA aptamers, Spiegelmers, RNA aptamers, organic molecules, proteins, protein fragments, oligopeptides, antibodies, and non-antibody scaffold proteins (e.g., transferrin, human tenth fibronectin type III domain, Z domain of *S. aureus* protein A, kunitz domain of a human trypsin inhibitor, ankyrin repeat protein, human lipocalcin, human crystalin, human ubiquitin, trypsin inhibitor from *E. elaterium*).

In some embodiments, the CXCL11 antagonist partially or completely blocks the interaction between CXCL11 and CXCR3 and/or CXCR7. In one embodiment, the CXCL11 antagonist is an antibody that specifically binds to CXCL11 and partially or completely blocks the interaction between CXCL11 and CXCR3 and/or CXCR7. In certain embodiments, the antibody binds to CXCL11 with a $K_D$ of $5\times10^{-8}$M or less, for example, $1\times10^{-8}$M or less, $1\times10^{-9}$ M or less, $1\times10^{-10}$ M or less, or $1\times10^{-11}$M or less. In some embodiments, the CXCL11 antagonist partially or completely blocks the CXCL11-mediated internalization of CXCR3 and/or CXCR7. Exemplary CXCL11 antagonists are described in, e.g., WO2003/106488 and WO2008/077945.

In some embodiments, the sMICA antagonist is an agent that reduces the level of sMICA. In other embodiments, the sMICA antagonist partially or completely blocks the interaction between sMICA and NKG2D. In one embodiment, the sMICA antagonist is an antibody that specifically binds to MICA (e.g., sMICA) and partially or completely blocks the interaction between sMICA and NKG2D. In certain embodiments, the antibody binds to MICA (e.g., sMICA) with a $K_D$ of $5\times10^{-8}$M or less, for example, $1\times10^{-8}$M or less, $1\times10^{-9}$M or less, $1\times10^{-10}$ M or less, or $1\times10^{-11}$M or less. In some embodiments, the sMICA antagonist partially or completely blocks the sMICA-mediated NKG2D internalization. In another embodiment, the sMICA antagonist partially or completely prevents shedding of sMICA from MICA. In a further embodiment, the antibody binds to the alpha 3 domain of MICA, and thus does not block NKG2D receptor binding. Exemplary antibodies that specifically bind to MICA (e.g., sMICA) are described, for example, in WO2014/144791.

Exemplary anti-CTLA-4 antibodies for use in anti-CTLA-4 immunotherapy include, for example, Yervoy™ (ipilimumab or antibody 10D1, described in PCT Publication WO 01/14424), tremelimumab (formerly ticilimumab, CP-675,206), or an anti-CTLA-4 antibody described in any of the following publications: WO 98/42752; WO 00/37504; U.S. Pat. No. 6,207,156; Hurwitz et al. *PNAS* 1998; 95:10067-71; Camacho et al. *J Clin Oncology* 2004; 22:Abstract No. 2505 (antibody CP-675206); and Mokyr et al. *Cancer Res* 1998; 58:5301-4. Any of the anti-CTLA-4 antibodies disclosed in WO2013/173223 may also be used. In certain embodiments, the anti-CTLA-4 antibody binds to human CTLA-4 with a $K_D$ of $5\times10^{-8}$M or less, for example, $1\times10^{-8}$ M or less, $1\times10^{-9}$M or less, $1\times10^{-10}$ M or less, or $1\times10^{-11}$ M or less.

Also provided herein are methods for screening agents that bind to CXCL11 or sMICA. For example, chemical libraries, peptide libraries, and or collections of natural products can be screened, using methods well-known in the art, for agents that bind to CXCL11 or sMICA.

In some embodiments, rational drug design is conducted based on the use of crystal or solution structural information on CXCL11 or sMICA.

CXCL11 or sMICA antagonists can be prepared by any known procedure in the art, including recombinant DNA-related technologies, and chemical synthesis technologies. Methods for generating monoclonal and polyclonal antibodies, as well as antigen-binding fragments thereof, to target antigens are also well-known in the art.

Agents identified to bind to CXCL11 or sMICA can be further tested for antagonist activity using art-recognized methods. Such methods include assays to determine whether the candidate CXCL11 or sMICA antagonist blocks the binding of CXCL11 to CXCR3 and/or CXCR7, or sMICA to NKG2D. In certain embodiments, a candidate CXCL11 antagonist is tested for its ability to reduce CXCR3 internalization and/or chemotaxis, as described in, e.g., Sauty et al., *J Imunol* 2001; 167:7084-93; Colvin et al., *JBC* 204; 279:30219-27). In other embodiments, a candidate sMICA antagonist is tested for its ability to reduce NKG2D internalization and/or NK cytotoxicity using the methods described in, e.g., Groh et al., *Nature* 2002; 419:734-8 and Ashiru et al., *Cancer Res* 2010: 70:481-9).

IV. Combination Therapies

Also provided herein are combination therapies for treating a cancer patient determined to have levels of CXCL11 and/or sMICA that are above the levels measured in healthy individuals (e.g., those without cancer and those who are not suspected as being at risk of developing cancer). In some embodiments, the level of CXCL11 in the cancer patient (e.g., in patient serum) is above about 35 pg/mL and/or the level of sMICA is above about 247 pg/mL, as assessed, e.g., using a bead-based immunoassay.

In one embodiment, the patient is administered an anti-CTLA-4 immunotherapy (e.g., ipilimumab or tremelimumab) and a CXCL11 antagonist and/or sMICA antagonist.

In another embodiment, the patient is administered a CXCL11 antagonist and/or sMICA antagonist.

In yet another embodiment, either of the above combination therapies includes administration of one or more additional therapeutic agents (e.g., simultaneous, separate, or sequential administration). Exemplary therapeutic agents administered in these combinations are described below.

In certain embodiments, the therapeutic agent is one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that modulate one of the above proteins include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), and Muromonab-CD3 (to CD3). In a preferred embodiment, a CXCL11 antagonist or sMICA antagonist is used in combination with ipilimumab.

Suitable anti-CTLA4 antibodies for use in combination therapies include an anti-CTLA-4 antibody described in any of the following publications: WO 98/42752; WO 00/37504; U.S. Pat. No. 6,207,156; Hurwitz et al., *PNAS* 1998; 95:10067-71; Camacho et al., *J Clin Oncology* 2004; 22:Abstract No. 2505 (antibody CP-675206); WO2013/173223, US2014/0105914, and Mokyr et al., *Cancer Res* 1998; 58:5301-4.

Suitable PD-1 antagonists for use in combination therapies include, for example, a PD-1-Fc fusion protein, such as AMP-244. In one embodiment, the PD-1 antagonist is an anti-PD-1 or anti-PD-L1 antibody. An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD1 antibody is MK-3475 (Lambrolizumab) described in WO2012/145493; and AMP-514 described in WO 2012/145493. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used. An anti-PD-1 antibody that competes for binding with, and/or binds to the same epitope on PD-1 as, as one of these antibodies may also be used in combination treatments. Another approach to target the PD-1 receptor is the recombinant protein composed of the extracellular domain of PD-L2 (B7-DC) fused to the Fc portion of IgG1, called AMP-224.

Exemplary PD-L1 antagonists suitable for use in combination therapies described herein include the anti-PD-L1 antibody BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiment an anti-PD-L1 antibody is MEDI4736 (also known as Anti-B7-H1), MPDL3280A (also known as RG7446), MSB0010718C (WO2013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used. Anti-PD-L1 antibodies that compete with and/or bind to the same epitope as that of any of these antibodies may also be used in combination treatments.

Exemplary anti-LAG3 antibodies suitable for use in combination therapies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273.

Exemplary anti-OX40 antibodies suitable for use in combination therapies include, e.g., MEDI-6383, MEDI-6469 or MOXR0916 (RG7888; WO06/029879).

Exemplary anti-CD137 (4-1BB) antibodies suitable for use in combination therapies include urelumab or PF-05082566 (WO12/32433).

Suitable CD40 agonists that can be used in combination therapies include, for example, lucatumumab (HCD122), dacetuzumab (SGN-40), CP-870,893 or Chi Lob 7/4.

Suitable anti-GITR antibodies that can be used in combination therapies include, e.g., an antibody having the CDR sequences of 6C8, e.g., a humanized antibody having the CDRs of 6C8, as described, e.g., in WO2006/105021; an antibody comprising the CDRs of an anti-GITR antibody described in WO2011/028683; an antibody comprising the CDRs of an anti-GITR antibody described in JP2008278814, or an antibody comprising the CDRs of an anti-GITR antibody described in WO2015/031667.

Other therapeutic agents include antagonists of inhibitory receptors on NK cells or agonists of activating receptors on NK cells (e.g., antagonists of KIR such as lirilumab).

In certain embodiments, the therapeutic agent is an (i) antagonist (or inhibitor or blocking agent) of a protein of the IgSF family or B7 family or the TNF family that inhibit T cell activation or an antagonist of a cytokine that inhibits T cell activation (e.g., IL-6, IL-10, TGF-β, VEGF; "immunosuppressive cytokines") and/or (ii) agonist of stimulatory receptors of the IgSF family, B7 family or the TNF family or of cytokines that stimulate T cell activation, for stimulating an immune response, e.g., for treating proliferative diseases, such as cancer.

Yet other agents suitable for use in combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Additional therapeutic agents include those that inhibit TGF-β signaling, such as GC1008, LY2157299, TEW7197, or IMC-TR1.

Another class of agents includes Toll-like receptor agonists, such as a TLR2/4 agonist (e.g., *Bacillus* Calmette-Guerin); a TLR7 agonist (e.g., Hiltonol® or Imiquimod); a TLR7/8 agonist (e.g., Resiquimod); or a TLR9 agonist (e.g., CpG7909).

Additional agents are those that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Therapies that may be used in combination therapies include those that deplete or block Treg cells, e.g., an agent that specifically binds to CD25.

Another agent for use in combination therapy is an agent that inhibits a metabolic enzyme such as indoleamine dioxigenase (IDO), dioxigenase, arginase, or nitric oxide synthetase.

Another class of agents for use in combination therapy includes agents that inhibit the formation of adenosine or inhibit the adenosine A2A receptor.

Yet another agent for use in combination therapy includes an IDO antagonist, such as INCB-024360 (WO2006/122150, WO07/75598, WO08/36653, WO08/36642), indoximod, NLG-919 (WO09/73620, WO09/1156652, WO11/56652, WO12/142237) or F001287.

Other therapies for use in combination include those that reverse/prevent T cell anergy or exhaustion and therapies that trigger an innate immune activation and/or inflammation at a tumor site.

The combination therapies disclosed herein may include one or more immuno-oncology agents, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Further therapeutic agents which can be included in the combination therapies described herein include one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In further embodiments, the combination therapies disclosed herein can be used with irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (TAXOL™), doxorubicin, 5-fu, or camptothecin+apo2l/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., Nat Med 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin®), synthetic triterpenoids (see Hyer et al., *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

In other embodiments, one or more anti-proliferative cytotoxic agents can be used in the combination therapies. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Anti-proliferative agents suitable for use in the combination therapies include, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the combination therapies disclosed herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

V. Compositions

Compositions provided herein include one or more therapeutic agents selected from a anti-CTLA-4 immunotherapeutic (e.g., antibody), a CXCL11 antagonist, and/or a sMICA antagonist, optionally formulated together with a pharmaceutically acceptable carrier.

The compositions may include additional therapeutic agents, as discussed above. For example, the composition can include an CXCL11 antagonist, sMICA antagonist, and/or anti-CTLA-4 immunotherapy, combined with at least one other anti-cancer and/or T-cell stimulating (e.g., activating) agent.

In some embodiments, the compositions includes other compounds, drugs, and/or agents used for the treatment of cancer. Such compounds, drugs, and/or agents can include, for example, chemotherapy drugs, small molecule drugs, or antibodies that stimulate the immune response to a given cancer.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for oral, intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The pharmaceutical compositions described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19).

The pharmaceutical compositions also may include a pharmaceutically acceptable anti-oxidant, such as a water soluble antioxidant, oil-soluble antioxidant, or metal chelating agent.

Examples of suitable aqueous and nonaqueous carriers include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions may also contain an effective amount of an adjuvant, preservative, wetting agent, emulsifying agent, and/or dispersing agent. In this context, an "effective amount" of a preservative refers to an amount sufficient to prevent the active ingredient from degrading, relative to the active ingredient in the absence of a preservative, for a certain duration (e.g., at least 2 weeks, such as at least 3 weeks, at least 1 month, at least 2 months, at least 4 months, at least 6 months, at least 1 year, or at least 2 years). Prevention of presence of microorganisms may be ensured both by sterilization procedures, and by the inclusion of various antibacterial and antifungal agents, for example, paraben, chlorobutanol, phenol sorbic acid, and the like. In certain embodiments, isotonic agents, such as sugars, sodium chloride, and the like, are included in the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of an CXCL11 antagonist, sMICA antagonist, and/or anti-CTLA-4 immunotherapy (e.g., ipilimumab), the dosage ranges from about 0.0001 to 100 mg/kg, and more usually 0.01 to 5 or 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

In some embodiments, the CXCL11 antagonist, sMICA antagonist, and/or anti-CTLA-4 immunotherapy may be administered at a flat dose (flat dose regimen).

When the antagonist is an antibody, in some embodiments, two or more monoclonal antibodies with different binding specificities are administered simultaneously, in which case the dosage of each antibody administered falls within the ranges indicated. Antibodies are typically administered on multiple occasions. Intervals between single dosages can be, for example, weekly, monthly, every three months or yearly. Intervals can also be irregular as indicated by measuring blood levels of antibody to the target antigen in the patient. In some embodiments, the dosage is adjusted to achieve a plasma antibody concentration of about 1-1000 µg/ml, and in particular embodiments, about 25-300 µg/ml.

In some embodiments, the CXCL11 antagonist, sMICA antagonist, and/or anti-CTLA-4 immunotherapy is administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a CXCL11 antagonist, sMICA antagonist, and/or anti-CTLA-4 immunotherapy preferably results in a decrease in severity of disease symptoms, an increase in frequency and duration of disease symptom-free periods, or a prevention of impairment or disability due to the disease affliction. In the context of cancer, a therapeutically effective dose preferably results in increased survival (e.g., increased overall survival), and/or prevention of further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose may prevent or delay onset of cancer, such as may be desired when early or preliminary signs of the disease are present. Laboratory tests utilized in the diagnosis of cancer include chemistries, hematology, serology, and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

VI. Kits

Also provided herein are kits which include one or more agents for detecting and/or determining levels of CXCL1 and/or sMICA, optionally in combination with one or more therapeutic agents (e.g., anti-CTLA-4 immunotherapies and/or CXCL11 antagonists and/or sMICA antagonists), and instructions for use. Accordingly, in some embodiments, the kit comprises agents that bind to and detect CXCL11 and/or bind to and detect sMICA. In one embodiment, the binding agent is an antibody, or antigen-binding portion thereof.

Such kits may comprise at least one additional reagent. For example, the kits may comprise buffers, stabilizers, substrates, detection reagents, and/or cofactors required for the assay. In some embodiments, the binding agent and, optionally the reagents, are suitably aliquoted. In other embodiments, the kit comprises a means for obtaining the biological sample from a cancer patient. Such means can comprise, for example, reagents that can be used to obtain fluid or tissue sample from the cancer patient, The present disclosure is further illustrated by the following examples, which should not be construed as further limiting. The contents of all figures and all references, Genbank sequences, and patents and published patent applications cited throughout this application are expressly incorporated herein by reference.

EXAMPLES

Materials and Methods

To identify candidate soluble factor(s) that predict improved overall survival following ipilimumab treatment, pretreatment sera from treatment (ipilimumab) and "active control" (gp100 vaccine) patients from the phase 3 clinical trial of ipilimumab were analyzed for a variety of factors and their levels were correlated with OS. Candidate biomarkers were selected and each analyte was assessed in univariate and multivariate models for correlation with OS. Correlative biomarkers identified in the initial screen were further validated by testing sera from an independent cohort of ipilimumab-treated patients.

Clinical Trials

Detailed information regarding the phase 3 clinical trial of ipilimumab (NCT00094653) can be found in Hodi et al., *NEJM* 2010; 363:711-23. Patients with metastatic melanoma having failed at least one prior therapy that may have included interleukin-2 (IL-2), dacarbazine, and/or temozolomide were enrolled, excluding those with ocular melanoma. All patients were HLA-A*0201$^+$ as the restricting element for the gp100 peptides employed. All ipilimumab-treated patients received ipilimumab alone at 3 mg/kg every 3 weeks for 4 treatments. In the gp100 group, patients received two peptides (1 mg each), injected subcutaneously as an emulsion with incomplete Freund's adjuvant (Montanide™ ISA-51). Peptide injections were given immediately after a 90-minute intravenous infusion of placebo. Tumor burden was assessed by the treating physician.

Serum samples were also obtained from patients treated on an expanded access program at the Earle A. Chiles Research Institute (EACRI cohort). Detailed information regarding this Compassionate Use Trial for Unresectable Melanoma with Ipilimumab is available at ClinicalTrials.gov under the identifier NCT00495066. All patients received ipilimumab alone (3 mg/kg or 10 mg/kg every 3 weeks for 4 treatments), with no exclusions for ocular primary melanomas or HLA type.

Serum Cytokine Analysis

Serum was collected and stored at −80° C. until use. Chemokine (C-C motif) ligand 2 (CCL2), CCL3, CCL4, CCL8, CCL18, CCL26, chemokine (C-X-C motif) ligand 9 (CXCL9), CXCL10, CXCL11, CXCL13, and vascular endothelial growth factor (VEGF) were measured using a bead-based multiplexed immunoassay (R&D Systems, Minneapolis, Minn.). Soluble MHC class I polypeptide-related sequence A (sMICA), sMICB, soluble UL16 binding protein (sULBP)-1, sULBP-2, sULBP-3, and sULBP-4 were measured using a custom multiplex bead array (R&D Systems). Bead-based immunoassays were analyzed using the Luminex-based Bio-Plex system (BIO-RAD, Hercules, Calif.). Soluble CD25 (sCD25) and soluble lymphocyte-activation gene 3 (sLAG-3) were measured by ELISA (R&D Systems). Serum sHLA-G was measured by ELISA (Exbio Vestec, Czech Republic). Only serum cytokines having statistical significance in univariate analyses of overall survival (OS) were reported.

Statistical Considerations

Differences in baseline characteristics between treatment groups (ipilimumab vs. gp100) or trials (phase 3 vs compassionate use) were evaluated using a t-test for age and chi-square tests for gender, Eastern Cooperative Oncology Group (ECOG) performance status, lactate dehydrogenase (LDH), prior IL-2 therapy, and prior immunotherapy. Differences in baseline serum biomarkers between study and treatment groups were tested with Wilcoxon rank sum tests due to skewed distributions.

Analysis of OS was conducted in the phase 3 trial and separately in the confirmatory EACRI cohort due to differences in the patient populations, study design, and study protocol. In the phase 3 trial, differences within treatment groups were of primary interest and thus tested in separate models. Survival was defined as the time from initiating ipilimumab treatment to date of death, censoring a date of last follow-up. To calculate median follow-up time, deaths were censored.

Univariate survival analysis was performed for each treatment subgroup using Cox proportional hazards regression. Effects of CXCL11, sMICA, sMICB, sCD25, VEGF, absolutely lymphocyte counts (ALC), tumor burden, and effect of LDH (≤ vs >Upper Limit of Normal [ULN]) were shown. Models of quadratic effects to examine possible non-linear effects and models of linear effects of continuous variables were tested. When the quadratic effect was not significant or the linear effect was more strongly significant, main effects model results were reported. For sMICA and VEGF, the quadratic effect was significant in some models. In order to present a hazard ratio, results were also reported for a categorized variable, with the cut point determined as the quintile where a threshold effect was observed in phase 3 trial. Kaplan-Meier plots used for determining cut points are shown (FIGS. 6A-6F). In multivariate analyses, model results of the remaining variables (other than sMICA), however, are from the model containing the continuous form of the variable with the quadratic effect. Continuous measures were approximately log normal and analyzed as log base 10 transformed.

In multivariate analysis of OS, Cox proportional hazards regression was used to test the effects of biomarker candidates on survival after adjusting for other biomarkers and baseline patient characteristics. Only CXCL11 and sMICA were included as they were significant in univariate survival models of the ipilimumab group, but not the gp100 group. Covariates in models for both studies were age, gender ECOG status, prior immunotherapy, LDH, and ALC. Tumor burden was also included in the multivariate model for the phase 3 trial cohort, but not the EACRI cohort, as these data were not captured.

Analyses were performed using SAS 9.3 (SAS Institute Inc., Cary, N.C.). Forest plots were prepared using Forest Plot Viewer and edited using Adobe Illustrator (San Jose, Calif.). Graph Pad Prism (La Jolla, Calif.) was used for depicting some Kaplan-Meier plots.

Example 1: Patient Characteristics of Phase 3 Study

Demographics for the phase 3 study were previously reported (Hodi et al., *NEJM* 2010; 363:711-23). Briefly, 676 patients were enrolled, and 137 were selected to receive ipilimumab monotherapy (treatment group), 136 to receive gp100 monotheraphy (control group), and 403 treated with the combination of these agents. Biomarker analysis was restricted to the monotherapy groups.

Baseline characteristics were similar between monotherapy groups (Table 1), except that a higher proportion of patients received prior immunotherapy in the gp100 alone groups (P=0.036) (Table 1, column D). Patients were followed for a median of 31 months (range, 27-43 months). Overall survival of the ipilimumab group was 45.6% at 12 months, 33.2% at 18 months, and 23.5% at 24 months, with a median overall survival of 10.1 months (95% CI, 8.0 to 13.8). Overall survival of the gp100 group was 25.3% at 12 months, 16.3% at 18 months, and 13.7% at 24 months, with a median overall survival of 6.4 months (95% CI, 5.5 to 8.7). Analysis of soluble immunomodulatory proteins was performed on serum collected prior to treatment. Baseline CXCL11 concentrations were comparable between ipilimumab (median 38, range 2-1027 pg/mL) and gp100 (median 39, range 2-911 pg/mL) groups. Similarly, baseline levels of sMICA were consistent between ipilimumab (median 115, range 13-1573 pg/mL) and gp100 (median 121, range 13-2074 pg/mL) groups.

while sMICB, sCD25, VEGF, LDH, tumor burden, and ALC represent putative prognostic biomarkers.

Multivariate analyses were also conducted with a focus on CXCL11 and sMICA, as these two biomarkers were identified in the univariate analysis as correlating with ipilimumab but not gp100 treatment. Models were used to test the independent effects of CXCL11 and sMICA after adjusting for each other and the covariates LDH, ALC, tumor burden, age, sex, and ECOG status. Within the ipilimumab-treated group, CXCL11 and LDH, but not tumor burden, ALC, age, sex, or ECOG score, were associated with OS ($\log_{10}$ CXCL11 HR, 1.88; 95% CI; 1.14 to 3.12; P=0.014: LDH

TABLE 1

| Demographic or Clinical Characteristic | A<br>Phase 3 trial cohort | B | C<br>EACRI cohort | D<br>Statistics | E |
|---|---|---|---|---|---|
| | Ipilimumab monotherapy (n = 124) | gp100 monotheraphy (n = 123) | Ipilimumab monotherapy (n = 48) | P* Value: A vs B | P* Value: A vs C |
| Age, years | | | | 0.99 | 0.51 |
| Median | 57 | 57 | 60 | | |
| Range | 23-90 | 19-88 | 36-81 | | |
| Male, % | 61.3 | 54.5 | 60.4 | 0.28 | 0.92 |
| ECOG, % | | | | .85** | .22** |
| 0 | 51.6 | 52.9 | 41.7 | | |
| 1 | 47.6 | 43.9 | 52.1 | | |
| 2 | 0.8 | 3.2 | 6.3 | | |
| LDH > ULN, % | 37.1 | 36.4 | 66 | 0.91 | 0.0007 |
| ALC, ×10$^9$/L | | | | 0.27 | 0.61 |
| Median | 1.3 | 1.2 | 1.3 | | |
| Range | 0.4-3.3 | 0.3-2.8 | 0.3-4.1 | | |
| Prior IL-2 therapy, % | 23.4 | 25.2 | 60.4 | 0.74 | <.0001 |
| Prior immunotherapy$^§$, % | 39.5 | 52.9 | 77.1 | 0.036 | <.0001 |
| CXCL11 (pg/mL) | | | | 0.51 | 0.0003 |
| Median | 38 | 39 | 14 | | |
| Range | 2-1027 | 2-911 | 3-153 | | |
| sMICA (pg/mL) | | | | 0.99 | <.0001 |
| Median | 115 | 121 | 299 | | |
| Range | 13-1573 | 13-2074 | 12-2546 | | |
| Median survival$^#$, months | 10.1 | 6.9 | 8.6 | | |

Abbreviations: ECOG, Eastern Cooperative Oncology Group performance status; ULN, upper limit of normal; LDH, Lactate dehydrogenase; IL-2, interleukin-2.
*P-values shown from t-test for age, Wilcoxon log rank test for CXCL11 and sMICA, and Chi-square tests for all other variables.
**ECOG 1-2 vs 0  $^§$Including IL-2  $^#$Median survival times calculated from Kaplan-Meier estimates.

Example 2: CXCL11, sMICA, and Overall Survival

Figure 2A:
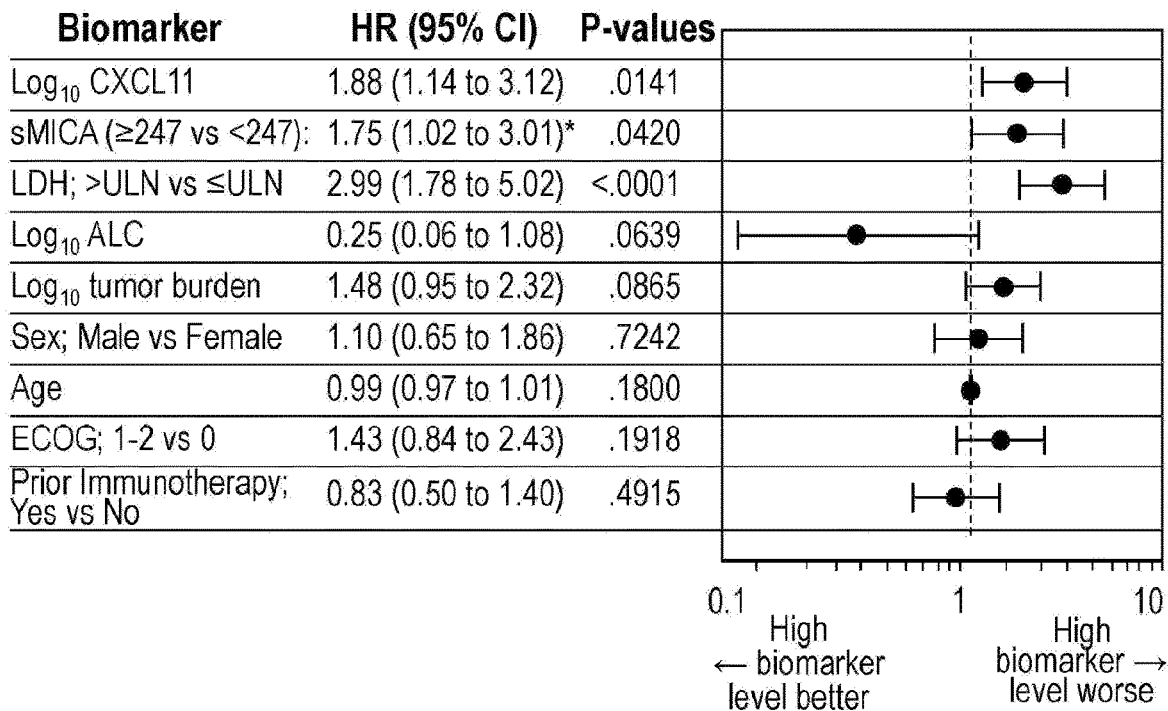
FIGS. 2A and 2B show the results of the multivariate analysis of biomarker effects on OS for patients from the phase 3 clinical trial. HRs and CIs are shown for the association of potential biomarkers with OS of patients treated with ipilimumab (FIG. 2A) or gp100 (FIG. 2B). Cox proportional hazards regression was used for multivariate analysis of biomarker effects on OS. Among the 113 total patients analyzed, 34 were censored in ipilimumab-treated group. Among total 115 patients analyzed, 13 were censored in gp100-treated group. * In quadratic effects model of ipilimumab group, $(\log_{10} \text{sMICA})^2$ P=0.0659.
Figure 2B:
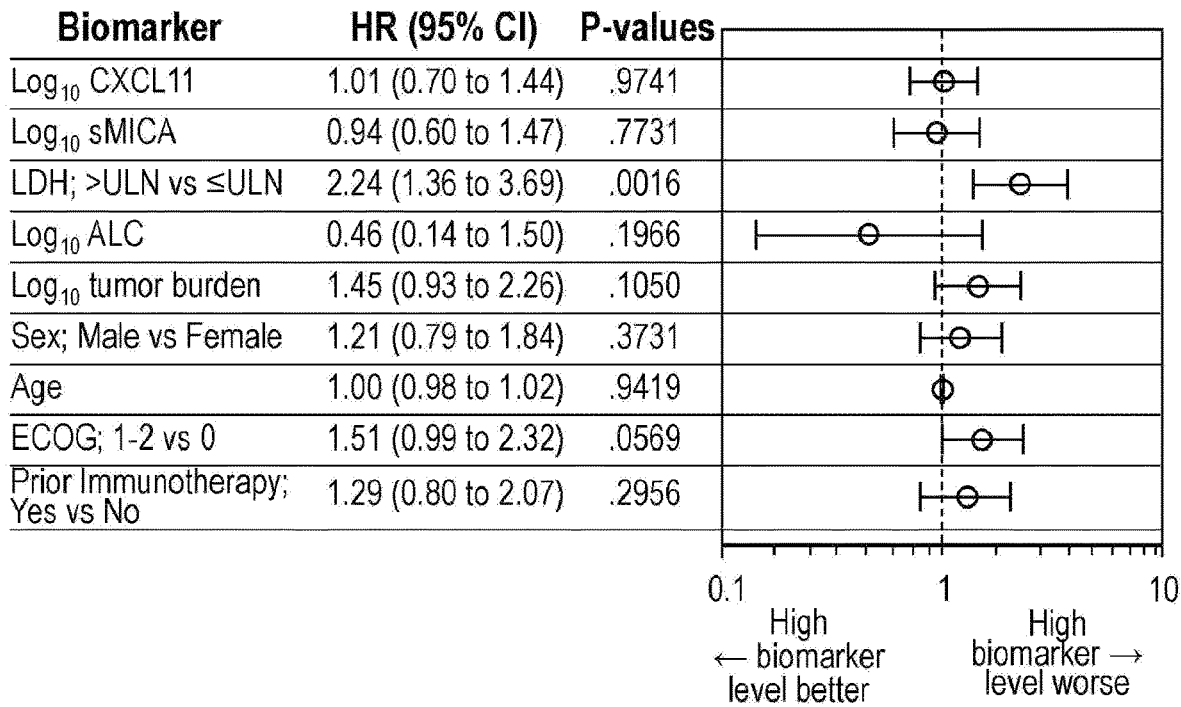

Univariate analysis of ipilimumab-treated patients showed that a 10-fold increase in CXCL11 was associated with double the risk of death (hazard ratio [HR], 2.08; 95% CI, 1.40 to 3.11; P=0.0003) (FIG. 1), whereas CXCL11 was not associated with OS in the gp100 group (HR, 1.21; 95% CI, 0.87 to 1.68; P=0.2597). The effect of CXCL11 on OS was significantly different for the ipilimumab group versus the gp100 group (P=0.040). In the univariate analysis of $\log_{10}$ sMICA, higher sMICA was associated with decreased survival in the ipilimumab group ($\log_{10}$ sMICA quadratic effect P<0.0001; sMICA (≥247 vs <247): HR, 3.46; 95% CI, 2.16 to 5.56 with P<0.0001), but not in the gp100 group ($\log_{10}$ sMICA HR, 0.91; 95% CI, 0.61 to 1.36; P=0.6373). Elevated sMICB, LDH, tumor burden, and sCD25 were all associated with poorer survival regardless of treatment (FIG. 1). Elevated VEGF was also associated with decreased survival in both groups, though marginally so for the ipilimumab-treated group (FIG. 1). Higher numbers of lymphocytes (ALC) at baseline were associated with better OS in both treatment groups (FIG. 1). These univariate analyses suggest that CXCL11 and sMICA are potential predictors of overall survival in ipilimumab treated melanoma patients, HR, 2.99; 95% CI, 1.78 to 5.02; P<0.0001) (FIG. 2A). sMICA was also associated with OS ($\log_{10}$ sMICA quadratic effect P=0.0659; sMICA (≥247 vs <247): HR, 1.75; 95% CI, 1.02 to 3.01 with P=0.0420), but less strongly than CXCL11 (FIG. 2A). In the gp100-treated group, only LDH was independently associated with OS (LDH HR, 2.24; 95% CI, 1.36 to 3.69; P=0.0016 (FIG. 2B). These multivariate results again suggest that CXCL11 and sMICA are potential predictive biomarkers of overall survival in ipilimumab-treated melanoma patients, whereas LDH represents a prognostic biomarker for melanoma patients irrespective of treatment.

Example 3: CXCL11 and sMICA in an Independent Ipilimumab-Treated Cohort

Sera from melanoma patients (48 of 52, 92.3%) collected prior to treatment with ipilimumab in an expanded access program (EACRI cohort) was analyzed. When comparing patient characteristics between the ipilimumab-treated phase 3 trial cohort and the EACRI cohort, more patients in the EACRI cohort had elevated LDH (P=0.0007), prior IL-2 therapy (P<0.0001), and prior immunotherapy (P<0.0001) (Table 1, column A, C, and E). This comparison suggests that the EACRI cohort included more patients with advanced disease and poorer prognosis. This discrepancy may account for shorter median survival of the EACRI cohort (8.6 months) relative to that of ipilimumab-treated phase 3 trial cohort (10.1 months). In the EACRI cohort, median follow up was 39 months (range, 0.8-40 months).

Figure 3:
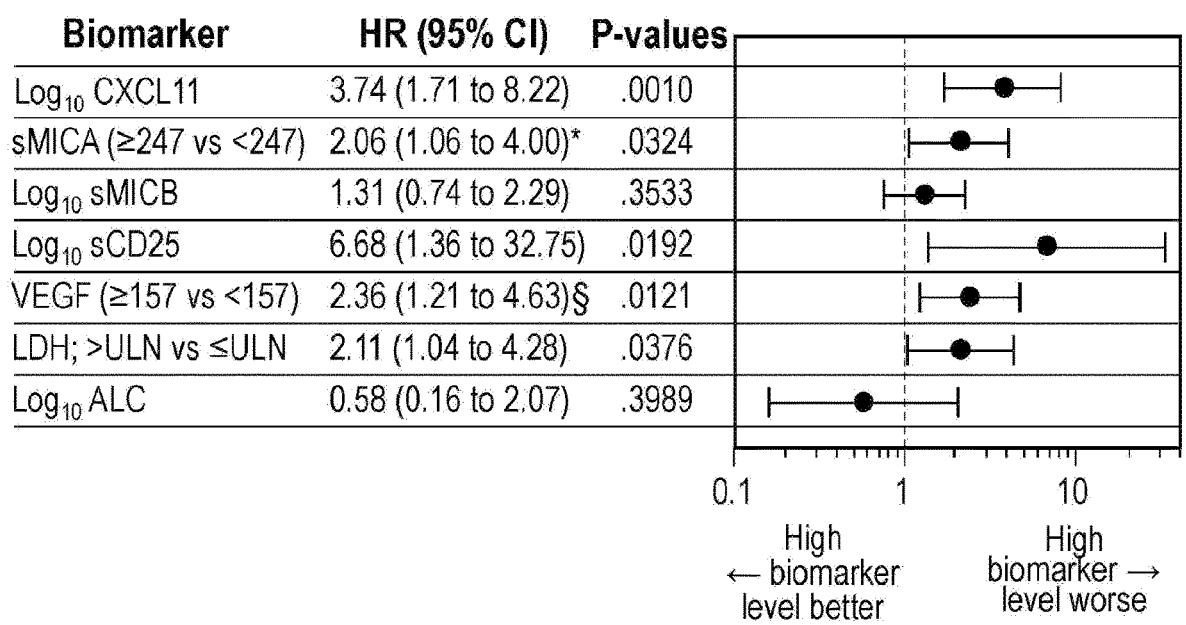
FIG. 3 shows the results of the univariate analysis of the ipilimumab-treated EACRI cohort. HRs and CIs are shown for the association of potential biomarkers with OS of patients treated with ipilimumab. Cox proportional hazards regression was used for univariate analysis of biomarker effects on OS. HR is numerator vs denominator. Among 48 total patients analyzed, 8 were censored. * In quadratic effects model, $(\log_{10} \text{sMICA})^2$ P=0.0244. § $(\log_{10} \text{VEGF})^2$ P=0.0200.
Figure 7A:
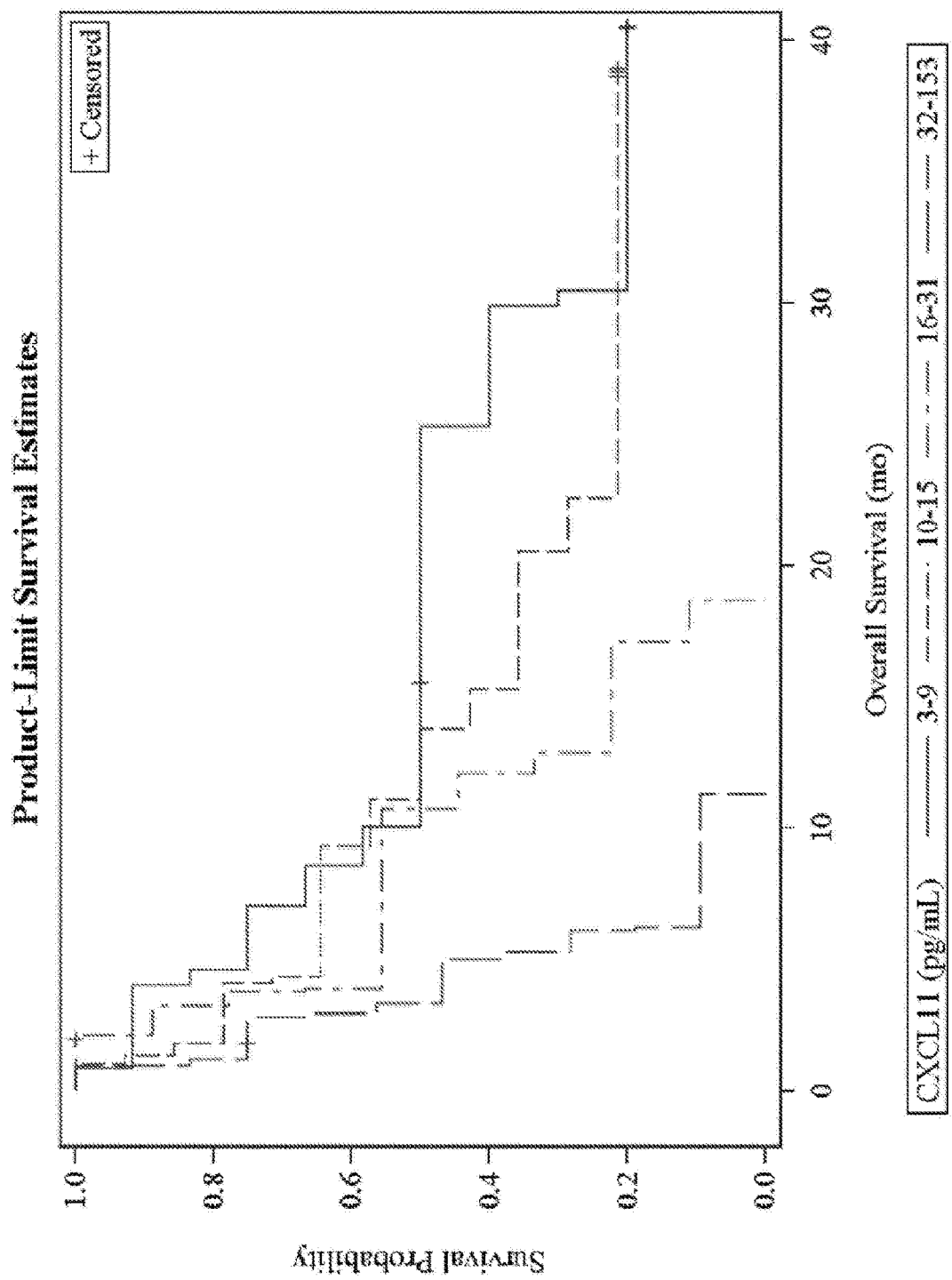
FIGS. 7A-7C are Kaplan-Meier plots depicting overall survival over 40 months based on concentration of the specified biomarker in the EACRI cohort.
Figure 7B:
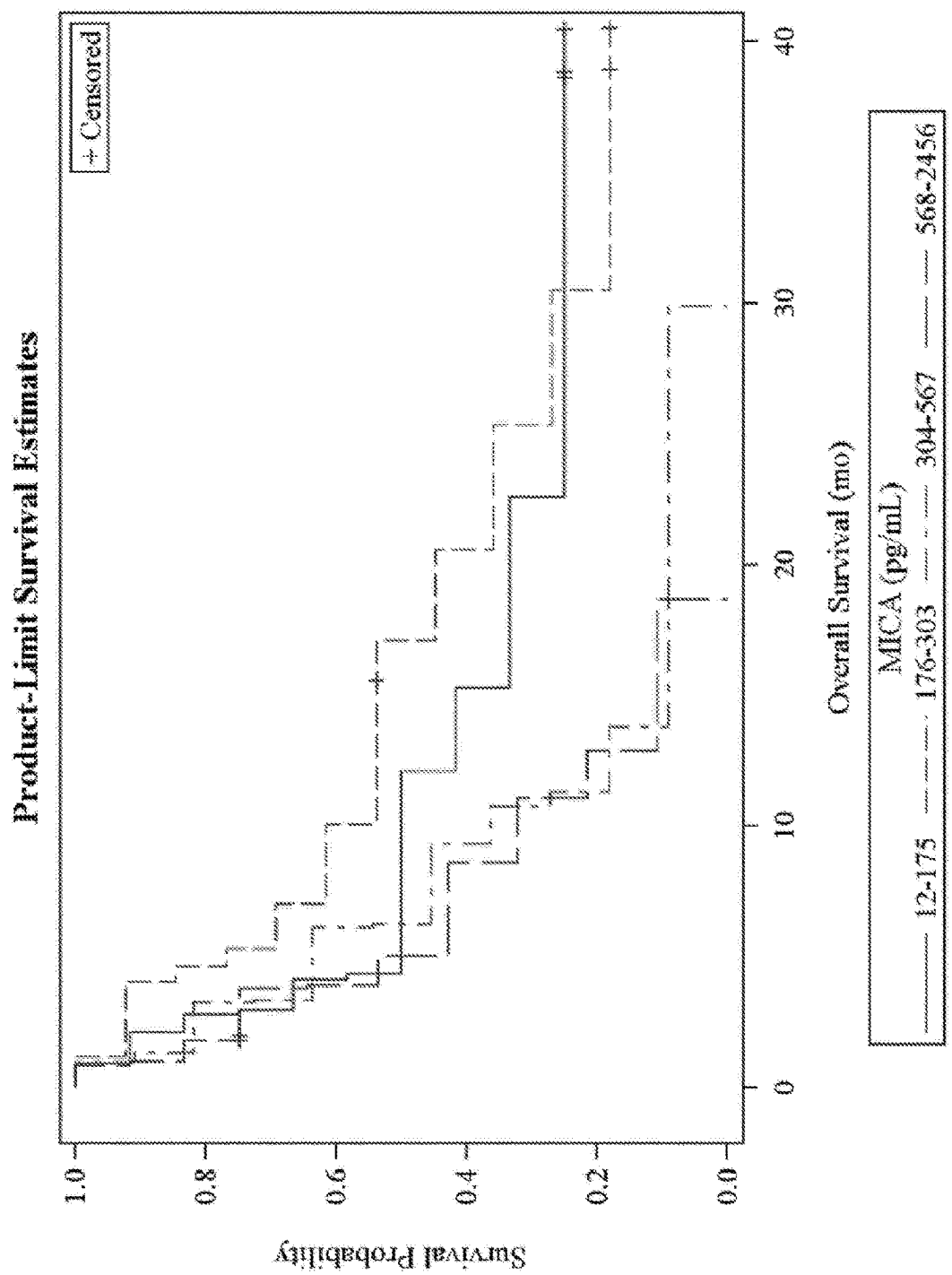
Figure 7C:
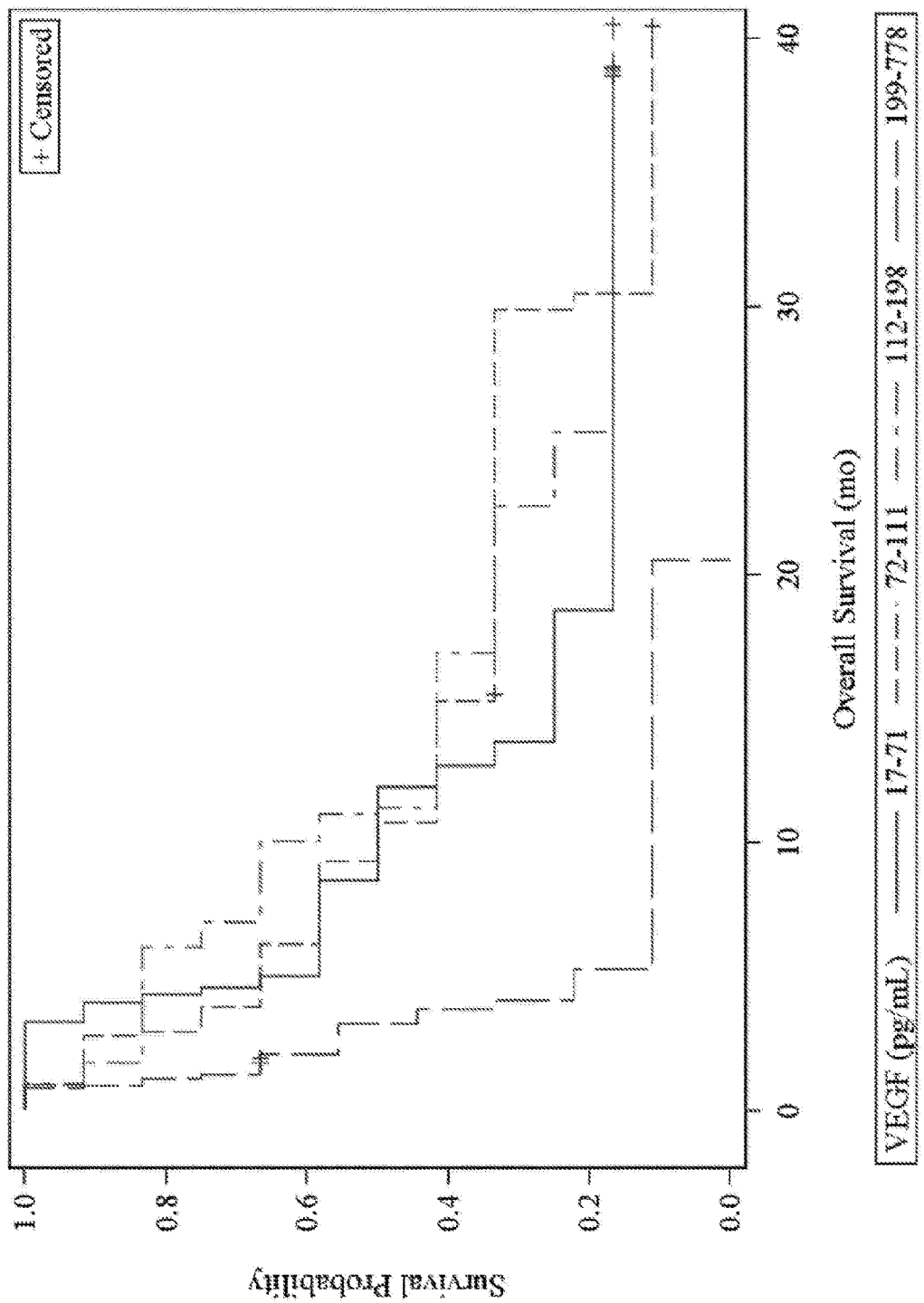

Univariate analyses showed that elevated pretreatment concentrations of CXCL11, sCD25, and LDH were associated with an increased risk of death (FIG. 3). Similar to phase 3 study findings, a 10-fold increase in CXCL11 was associated with a 3.7-fold increase in the risk of death (HR, 3.74; 95% CI, 1.71 to 8.22; P=0.0010). sMICA and VEGF effects were non-linear, depicted by the threshold effect as seen in the Kaplan-Meier plots of survival (FIGS. 7A-7C). Elevated sMICA was also associated with increased risk of death (log 10 sMICA quadratic effect P=0.0244; sMICA (≥247 vs <247): HR, 2.06; 95% CI, 1.06 to 4.00 with P=0.0324; FIG. 3). Elevated VEGF was associated with decreased survival and sMICB and ALC were not associated with survival.

Figure 4:
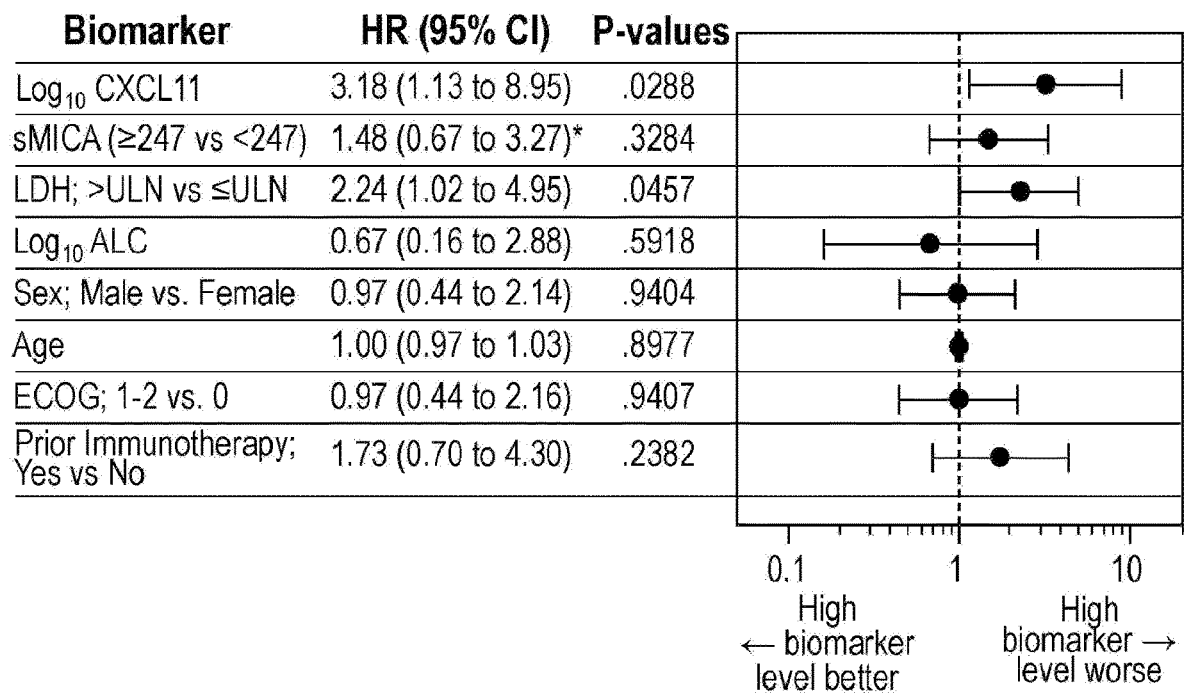
FIG. 4 shows the results of the multivariate analysis of the ipilimumab-treated EACRI cohort. HRs and CIs for the association of potential biomarkers with OS of patients treated with ipilimumab. Cox proportional hazards regression was used for multivariate analysis of biomarker effects on OS. HR is numerator vs denominator. Among 47 total patients analyzed, 8 were censored. * In quadratic effects model, $(\log_{10} \text{sMICA})^2$ P=0.1589.

Multivariate analysis showed that CXCL11 and LDH were associated with OS (log 10 CXCL11 HR, 3.18; 95% CI, 1.13 to 8.95; P=0.0288; and LDH HR, 2.24; 95% CI, 1.02 to 4.95; P=0.0457) after controlling for each other, gender, age, ECOG status, and prior immunotherapy (FIG. 4). sMICA may be associated with OS in this cohort (log 10 sMICA quadratic effect P=0.1589; sMICA (≥247 vs <247): HR, 1.48; 95% CI, 0.67 to 3.27 with P=0.3284; FIG. 4), a result due in part to adjusting for CXCL11 and LDH and somewhat small cohort size. Thus, the predictive association between CXCL11 and OS in ipilimumab-treated melanoma patients was confirmed, although there was a weaker association between sMICA and OS in the EACRI cohort. The association between LDH and OS in the EACRI cohort was also confirmed, compatible with the notion that LDH is a prognostic marker for patients with metastatic melanoma.

Example 4: Kaplan-Meier Survival Curves

Figure 5A:
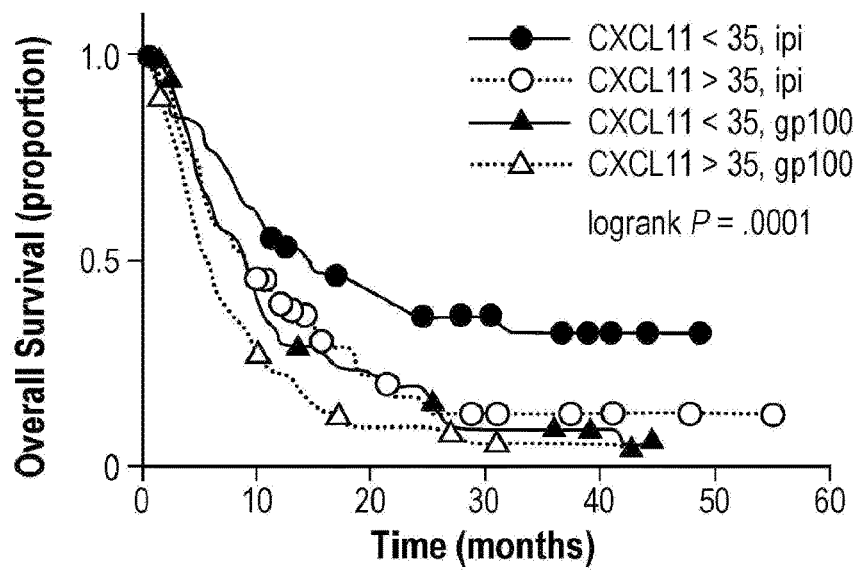
FIGS. 5A-5D show Kaplan-Meier curves for OS according to pretreatment CXCL11 or sMICA status. Curves for OS obtained by applying selected cut-off points for CXCL11 (FIG. 5A and FIG. 5C) and sMICA (FIG. 5B and FIG. 5D) to the phase 3 trial cohort (FIG. 5A and FIG. 5B) or the EACRI cohort (FIG. 5C and FIG. 5D). Numbers of subjects at risk at each 10 month interval are listed below each graph. The difference in treatment effect (ipilimumab (ipi) or gp100) according to CXCL11 or sMICA concentration is represented in the upper right of each graph (logrank).
Figure 5B:
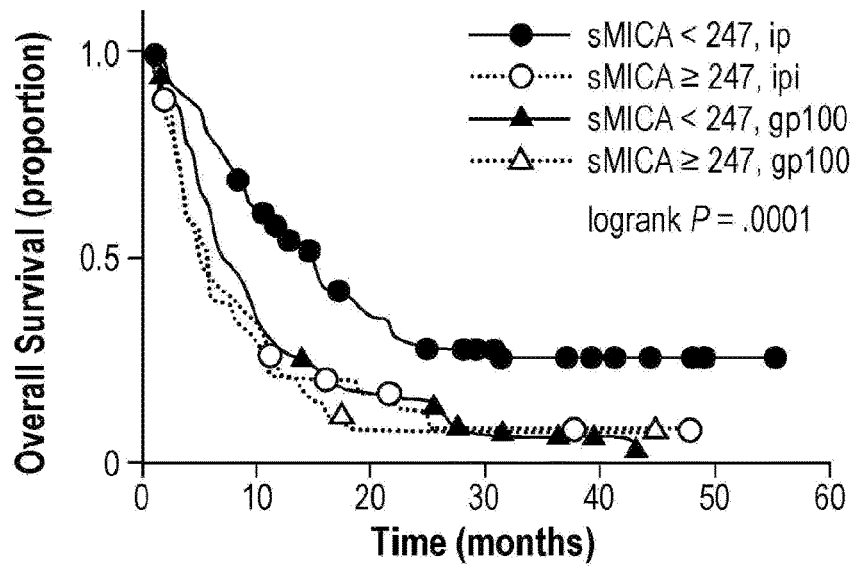
Figure 5C:
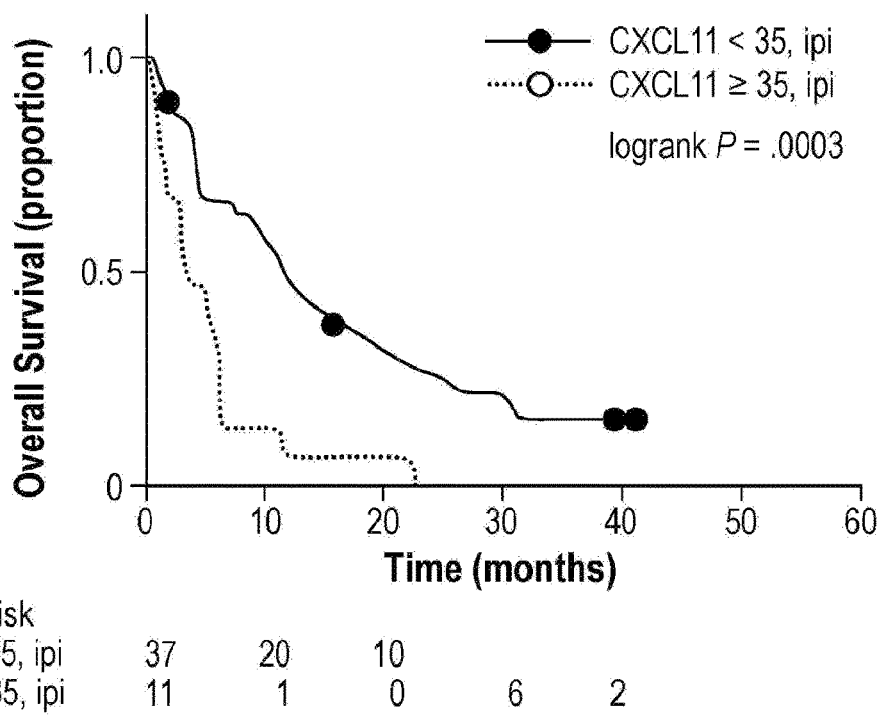
Figure 5D:
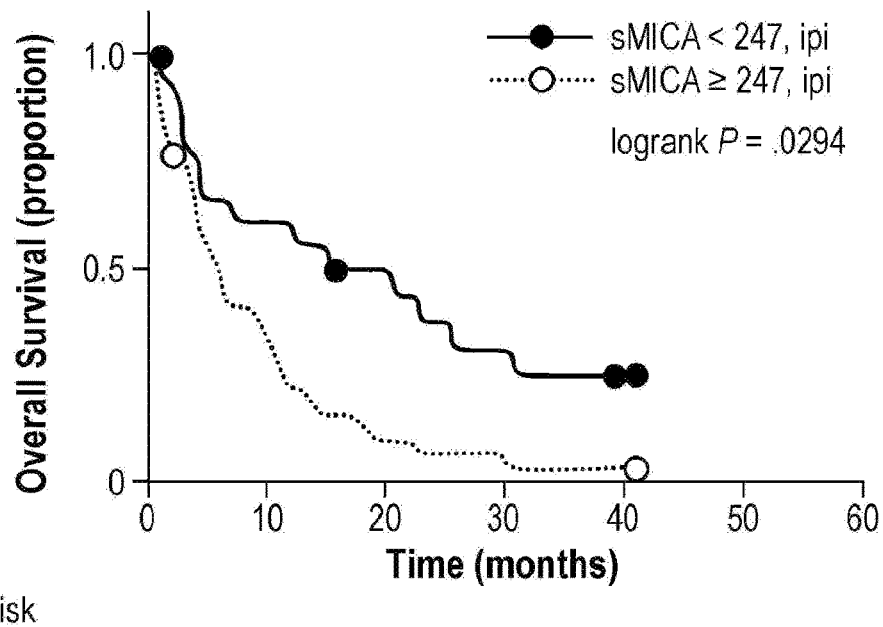
Figure 6A:
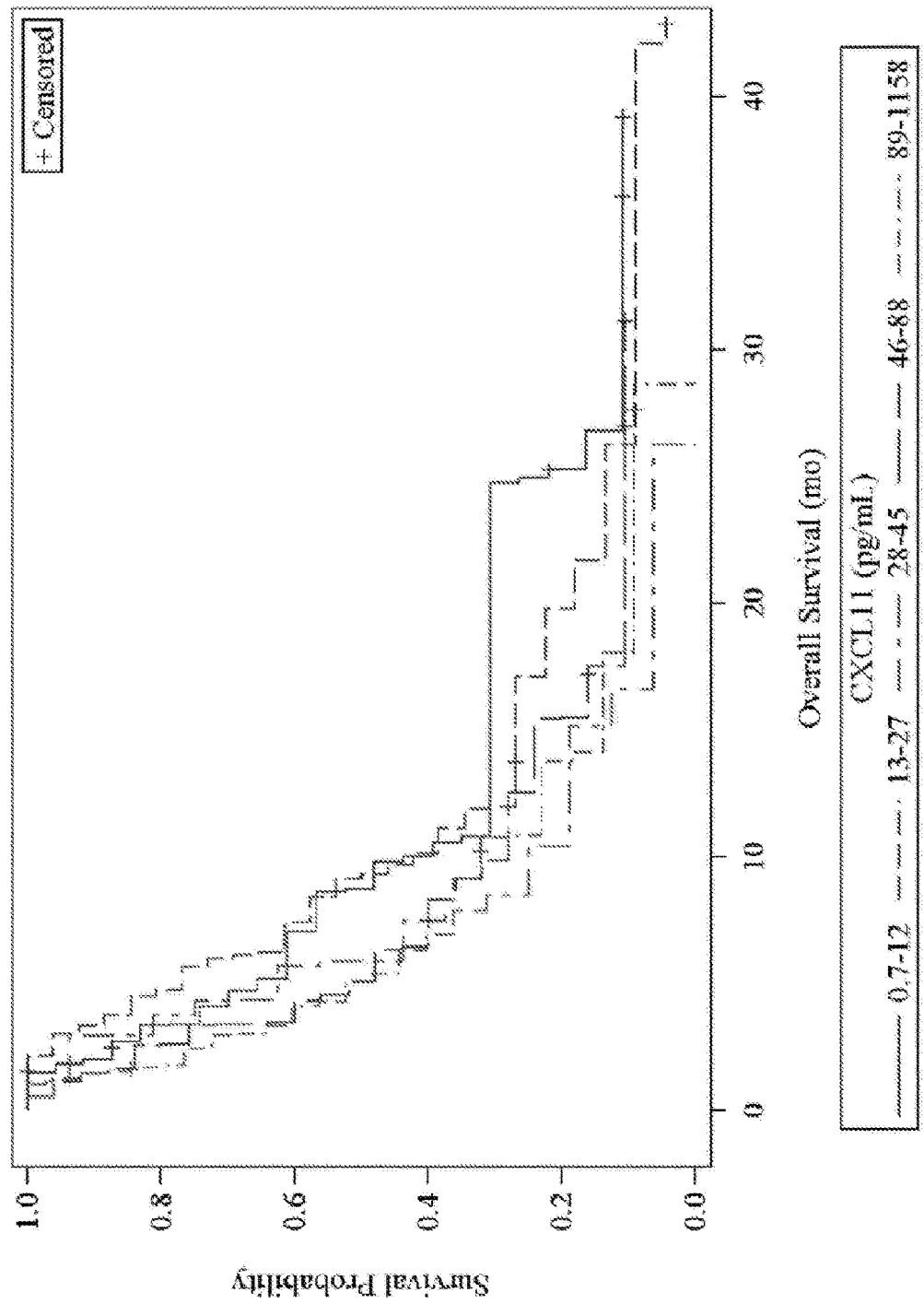
FIGS. 6A-6F show Kaplan-Meier curves for overall survival over 40-50 months based on concentration of the specified biomarker in the phase 3 clinical trial.
Figure 6B:
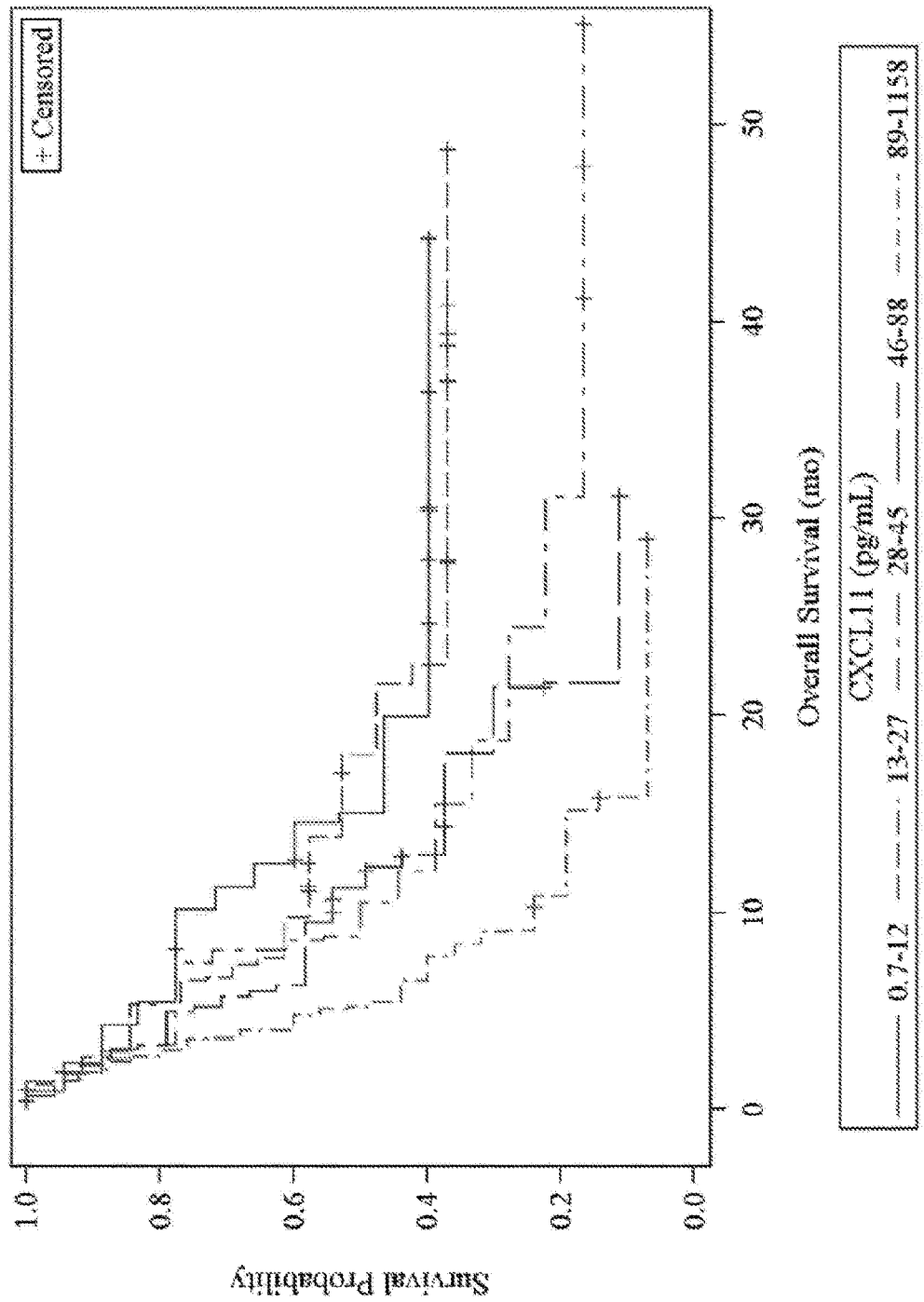
Figure 6C:
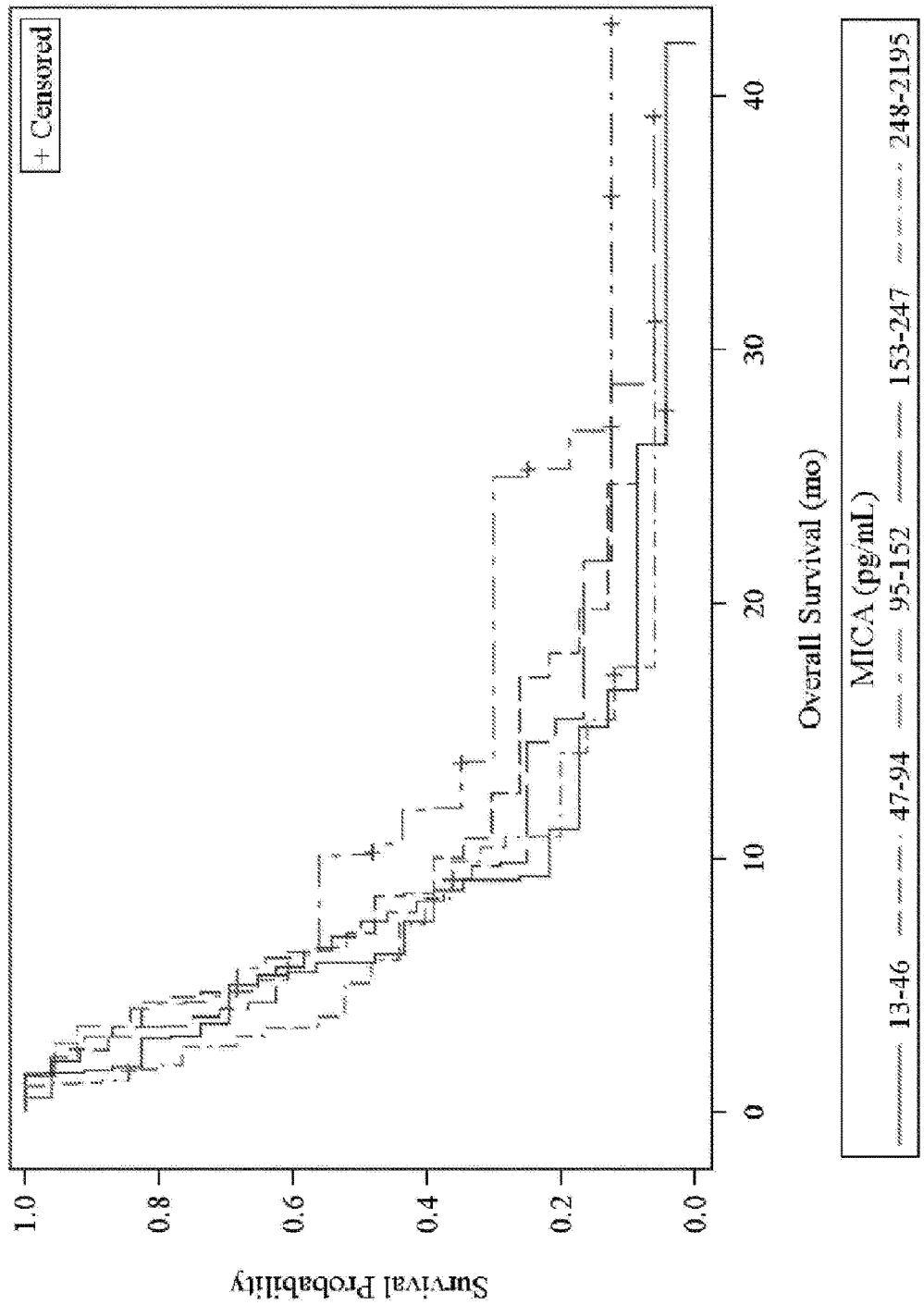
Figure 6D:
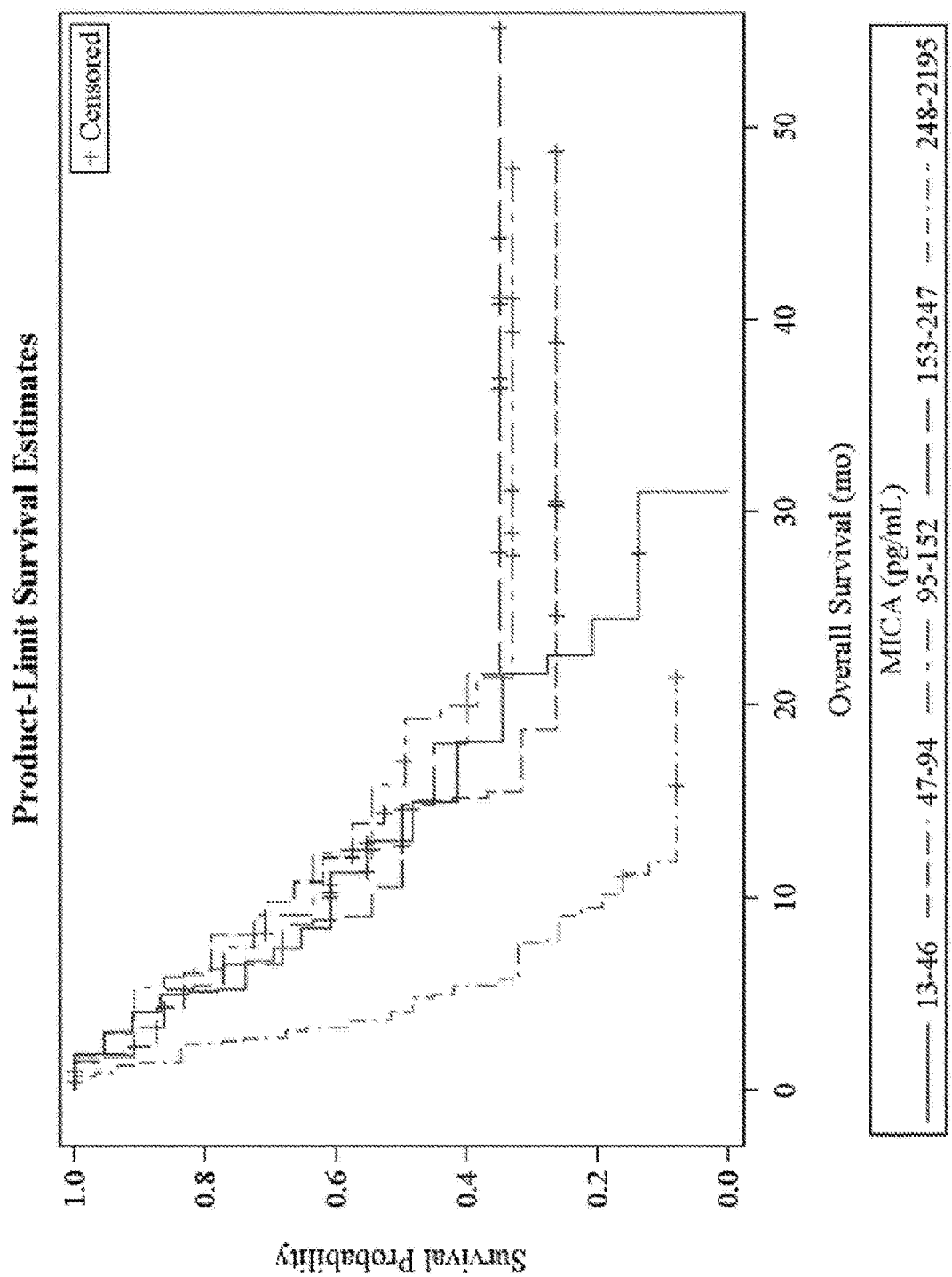
Figure 6E:
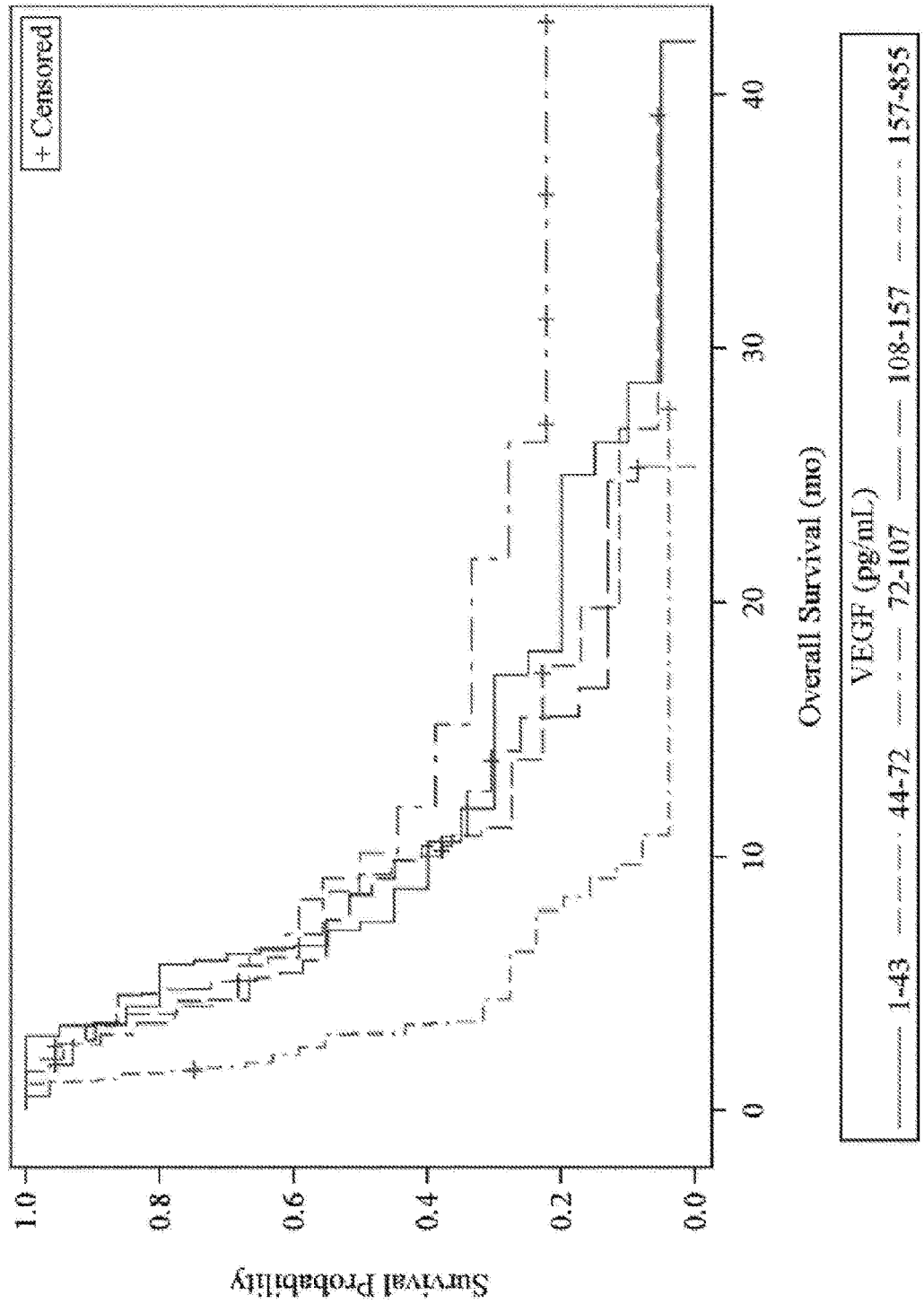
Figure 6F:
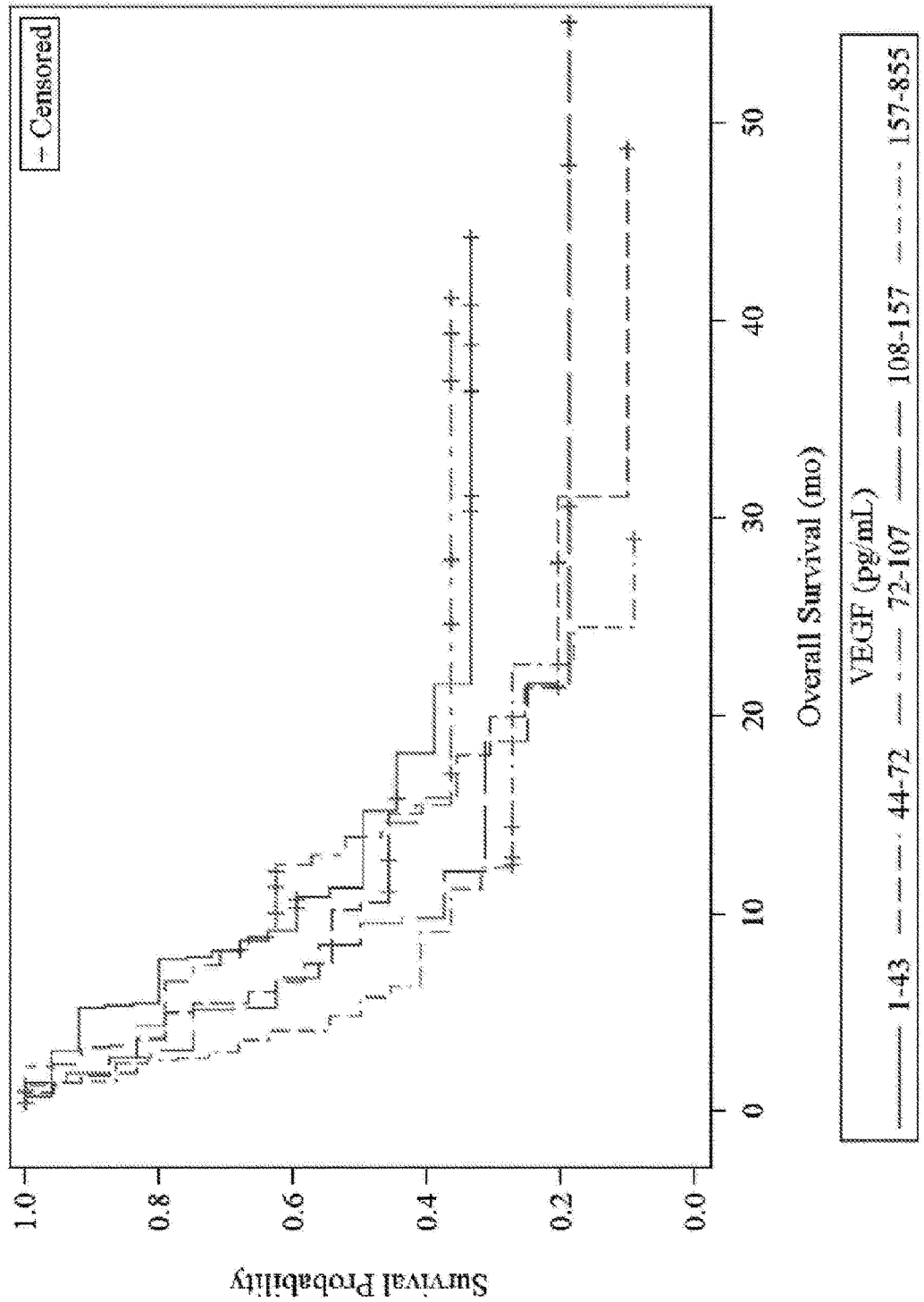

To illustrate the effects of CXC11 and sMICA on OS in the phase 3 trial, Kaplan-Meier survival plots were generated (FIGS. 5A-5D) for the biomarker high or low groups based on selected cut points (the median of CXC11; 35 pg/mL, the 80th percentile of sMICA; 247 pg/mL; FIGS. 5A and 5B). Due to the quadratic association of sMICA with survival, the 80th percentile was the cut point chosen based on the approximate threshold value seen in the sMICA quintile plot (FIGS. 6A-6F). Kaplan-Meier survival plots for the EACRI cohort were also generated using the same cut points as used for the phase 3 study data plot (FIGS. 5C and 5D). The distribution of baseline CXCL11 was lower and the distribution of sMICA levels higher in the confirmatory cohort (Table 1, column E). Nonetheless, both cut points successfully dichotomize patients treated with ipilimumab into patients with poor or better OS.

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of treating cancer in a patient with anti-CTLA-4 immunotherapy comprising:
   (a) determining the levels of CXCL11 in serum from the patient; and
   (b) if the levels of CXCL11 are below 35 pg/mL, then administering a therapeutically effective amount of an anti-CTLA4 immunotherapy, and if the levels of CXCL11 are at or above 35 pg/mL, then not treating the patient with an anti-CTLA4 immunotherapy, wherein the anti-CTLA4 immunotherapy comprises an antibody comprising the heavy and light chain variable region sequences set forth in SEQ ID NOs: 1 and 2, respectively, and wherein CXCL11 has the amino acid sequence set forth in SEQ ID NO: 3.

2. The method of claim 1, wherein the cancer is melanoma.

3. The method of claim 1, wherein the cancer is a metastatic cancer, refractory cancer, or recurrent cancer.

4. The method of claim 1, wherein the antibody is administered to the patient at between 1 mg/kg to 10 mg/kg.

5. The method of claim 1, wherein, if the patient is administered the antibody, then further administering to the patient one or more additional therapeutics.

6. The method of claim 1, wherein the patient has previously failed IL-2 therapy.

7. The method of claim 1, wherein the patient has previously failed dacarbazine therapy.

8. The method of claim 1, wherein the patient has previously failed temozolomide therapy.

9. A method of treating cancer comprising administering a therapeutically effective amount of an antibody comprising the heavy and light chain variable region sequences set forth in SEQ ID NOs: 1 and 2, respectively, to a patient identified as having serum levels of CXCL11 at or above 35 pg/mL, wherein CXCL11 has the amino acid sequence set forth in SEQ ID NO: 3.

10. The method of claim 9, wherein the cancer is melanoma.

11. The method of claim 9, wherein the cancer is a metastatic cancer, refractory cancer, or recurrent cancer.

12. The method of claim 9, wherein the antibody is administered to the patient at between 1 mg/kg to 10 mg/kg.

13. The method of claim 9, wherein the patient is further administered one or more additional therapeutics.

14. The method of claim 9, wherein the patient has previously failed IL-2 therapy.

15. The method of claim 9, wherein the patient has previously failed dacarbazine therapy.

16. The method of claim 9, wherein the patient has previously failed temozolomide therapy.

* * * * *

SEQUENCE LISTING

```
<160> NUMBER OF SEQ ID NOS: 3

<210> SEQ ID NO 1
<211> LENGTH: 116
<212> TYPE: PRT
<213> ORGANISM: Artificial Sequence
<220> FEATURE:
<223> OTHER INFORMATION: Synthetic: ipilimumab VH

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Arg Gln Ala Pro Gly Lys Gly Leu Glu Trp Val Thr Phe
        35                  40                  45

Ile Ser Tyr Asp Gly Asn Asn Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Ile Tyr Tyr Cys Ala Arg
                85                  90                  95

Thr Gly Trp Leu Gly Pro Phe Asp Tyr Trp Gly Gln Gly Thr Leu Val
            100                 105                 110

Thr Val Ser Ser
        115

<210> SEQ ID NO 2
<211> LENGTH: 108
```

```
<212> TYPE: PRT
<213> ORGANISM: Artificial Sequence
<220> FEATURE:
<223> OTHER INFORMATION: Synthetic: ipilimumab VL

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 3
<211> LENGTH: 94
<212> TYPE: PRT
<213> ORGANISM: Homo sapiens
<220> FEATURE:
<221> NAME/KEY: misc_feature
<223> OTHER INFORMATION: human CXCL11

<400> SEQUENCE: 3

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
        50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```